(12) United States Patent
Wang et al.

(10) Patent No.: US 12,377,173 B2
(45) Date of Patent: Aug. 5, 2025

(54) COMPOSITIONS COMPRISING HYPERPOLARIZED PROBES FOR $H_2O_2$ SENSING AND METHODS OF USING SAME

(71) Applicant: Duke University, Durham, NC (US)

(72) Inventors: Qiu Wang, Durham, NC (US); Hyejin Park, Durham, NC (US)

(73) Assignee: Duke University, Durham, NC (US)

( * ) Notice: Subject to any disclaimer, the term of this patent is extended or adjusted under 35 U.S.C. 154(b) by 746 days.

(21) Appl. No.: 17/744,128

(22) Filed: May 13, 2022

(65) Prior Publication Data

US 2022/0378952 A1 Dec. 1, 2022

Related U.S. Application Data

(60) Provisional application No. 63/188,797, filed on May 14, 2021.

(51) Int. Cl.
*A61K 49/10* (2006.01)
*C07F 5/04* (2006.01)

(52) U.S. Cl.
CPC .............. *A61K 49/106* (2013.01); *C07F 5/04* (2013.01)

(58) Field of Classification Search
CPC ....... A61K 49/106; A61K 49/10; C07F 5/025; C07F 5/04
See application file for complete search history.

(56) References Cited

U.S. PATENT DOCUMENTS

2006/0083688 A1* 4/2006 Singaram ................. B82Y 5/00
546/257

OTHER PUBLICATIONS

Lee et al., Macromolecules 1990, 23, p. 431-434. (Year: 1990).*
Ardenkjaer-Larsen, J. H.; Fridlund, B.; Gram, A.; Hansson, G.; Hansson, L.; Lerche, M. H.; Servin, R.; Thaning, M.; Golman, K., Increase in signal-to-noise ratio of > 10,000 times in liquid-state NMR. Proceedings of the National Academy of Sciences of the United States of America 2003, 100 (18), 10158-10163.
Barnham, K. J.; Masters, C. L.; Bush, A. I., Neurodegenerative diseases and oxidative stress. Nature Reviews Drug Discovery 2004, 3 (3), 205-214.
Bey Erik, A.; S. Bentle Melissa, E. Reinicke Kathryn, Y. Dong, C.-R. Yang, L. Girard, D. Minna John, G. Bornmann William, J. Gao, A. Boothman David, "An NQO1- and PARP-1-mediated cell death pathway induced in non-small-cell lung cancer cells by B-lapachone," PNAS 2007, 104, 11832-11837.
Brindle, K. M., Imaging Metabolism with Hyperpolarized 13C-Labeled Cell Substrates. Journal of the American Chemical Society 2015, 137 (20), 6418-6427.
Cheng, A. J.; Yamada, T.; Rassier, D. E.; Andersson, D. C.; Westerblad, H.; Lanner, J. T., Reactive oxygen/nitrogen species and contractile function in skeletal muscle during fatigue and recovery. The Journal of Physiology 2016, 594 (18), 5149-5160.
Colell, J.F., Logan, A.W., Zhou, Z., Shchepin, R.V., Barskiy, D.A., Ortiz Jr, G.X., Wang, Q., Malcolmson, S.J., Chekmenev, E.Y., Warren, W.S. and Theis, T., 2017. Generalizing, extending, and maximizing nitrogen-15 hyperpolarization induced by parahydrogen in reversible exchange. The Journal of Physical Chemistry C, 2017, 121 (12), pp. 6626-6634.
Comment, A., Dissolution DNP for in vivo preclinical studies. Journal of magnetic resonance (San Diego, Calif. : 1997) 2016, 264, 39-48.
Comment, A.; Merritt, M. E., Hyperpolarized Magnetic Resonance as a Sensitive Detector of Metabolic Function. Biochemistry 2014, 53 (47), 7333-7357.
D'Autréaux, B.; Toledano, M. B., ROS as signalling molecules: mechanisms that generate specificity in ROS homeostasis. Nature Reviews Molecular Cell Biology 2007, 8 (10), 813-824.
Dickinson, B. C.; Huynh, C.; Chang, C. J., A Palette of Fluorescent Probes with Varying Emission Colors for Imaging Hydrogen Peroxide Signaling in Living Cells. J Am Chem Soc 2010, 132 (16), 5906-5915.
Dickinson, B. C.; Chang, C. J., Chemistry and biology of reactive oxygen species in signaling or stress responses. Nature Chemical Biology 2011, 7 (8), 504-511.
Giorgio, M.; Trinei, M.; Migliaccio, E.; Pelicci, P. G., Hydrogen peroxide: a metabolic by-product or a common mediator of ageing signals? Nature Reviews Molecular Cell Biology 2007, 8 (9), 722-728.
Guo, H.; Aleyasin, H.; Dickinson, B. C.; Haskew-Layton, R. E.; Ratan, R. R., Recent advances in hydrogen peroxide imaging for biological applications. Cell & Bioscience 2014, 4 (1), 64.
Gutte, H.; Hansen, A. E.; Johannesen, H. H.; Clemmensen, A. E.; Ardenkjær-Larsen, J. H.; Nielsen, C. H.; Kjær, A., The use of dynamic nuclear polarization (13)C-pyruvate MRS in cancer. Am J Nucl Med Mol Imaging 2015, 5 (5), 548-560.
Hurd, R. E.; Yen, Y.-F.; Chen, A.; Ardenkjaer-Larsen, J. H., Hyperpolarized 13C metabolic imaging using dissolution dynamic nuclear polarization. Journal of Magnetic Resonance Imaging 2012, 36 (6), 1314-1328.
ISMRM 2022 Conference Abstract (submitted Nov. 10, 2021, Conference was May 7-12, 2022, when were abstracts made available?) Hyperpolarized 15N-BBCP as a novel probe of H2O2 ; Hyejin Park, Jun Chen, Ivan E. Dimitrov, Jae Mo Park, Qiu Wang.
Jing, X.; Yu, F.; Lin, W., A pet-based lysosome-targeted turn-on fluorescent probe for the detection of h2s and its bioimaging application in living cells and zebrafish. New Journal of Chemistry 2019, 43 (43), 16796-16800.

(Continued)

*Primary Examiner* — Michael G. Hartley
*Assistant Examiner* — Leah H Schlientz
(74) *Attorney, Agent, or Firm* — Quarles & Brady, LLP

(57) ABSTRACT

Provided are molecular probes for hyperpolarized $^{15}N$ magnetic resonance spectroscopic imaging (MRSI) and their use for detecting reactive species (e.g., hydrogen peroxide) and imaging of oxidative stress. In particular, $^{15}N$-boronobenzyl-4-cyanopyridinium ($^{15}N$-BBCP) demonstrated highly favorable physicochemical and hyperpolarization properties, including long spin-lattice relaxation time ($T_1$) and distinguishable $^{15}N$ chemical shift signals, that make it an effective reaction-based sensing probe for non-invasive, real-time detection of $H_2O_2$.

22 Claims, 14 Drawing Sheets

(56) References Cited

OTHER PUBLICATIONS

Keshari, K. R.; Wilson, D. M., Chemistry and biochemistry of 13C hyperpolarized magnetic resonance using dynamic nuclear polarization. Chemical Society Reviews 2014, 43 (5), 1627-1659.

Keshari, K.R., Kurhanewicz, J., Jeffries, R.E., Wilson, D.M., Dewar, B.J., Van Criekinge, M., Zierhut, M., Vigneron, D.B. and Macdonald, J.M., 2010. Hyperpolarized 13C spectroscopy and an NMR-compatible bioreactor system for the investigation of real-time cellular metabolism. Magnetic Resonance in Medicine: An Official Journal of the International Society for Magnetic Resonance in Medicine, 63(2), pp. 322-329.

Kim, G. H.; Kim, J. E.; Rhie, S. J.; Yoon, S., The Role of Oxidative Stress in Neurodegenerative Diseases. Experimental neurobiology 2015, 24 (4), 325-340.

Kondo, Y.; Nonaka, H.; Takakusagi, Y.; Sando, S., Design of Nuclear Magnetic Resonance Molecular Probes for Hyperpolarized Bioimaging. Angewandte Chemie International Edition 2020, 60, 27, p. 14779-14799. 10.1002/anie.201915718.

Kumar, N., Bhalla, V. and Kumar, M., 2015. Development and sensing applications of fluorescent motifs within the mitochondrial environment. Chemical Communications, 51(86), 2015, pp. 15614-15628.

Kurhanewicz, J.; Vigneron, D. B.; Ardenkjaer-Larsen, J. H.; Bankson, J. A.; Brindle, K.; Cunningham, C. H.; Gallagher, F. A.; Keshari, K. R.; Kjaer, A.; Laustsen, C.; Mankoff, D. A.; Merritt, M. E.; Nelson, S. J.; Pauly, J. M.; Lee, P.; Ronen, S.; Tyler, D. J.; Rajan, S. S.; Spielman, D. M.; Wald, L.; Zhang, X.; Malloy, C. R.; Rizi, R., Hyperpolarized (13)C MRI: Path to Clinical Translation in Oncology. Neoplasia (New York, N.Y.) 2019, 21 (1), 1-16.

Liou, G.-Y.; Storz, P., Reactive oxygen species in cancer. Free Radic Res 2010, 44 (5), 479-496.

Lippert, A. R.; Keshari, K. R.; Kurhanewicz, J.; Chang, C. J., A Hydrogen Peroxide-Responsive Hyperpolarized C-13 MRI Contrast Agent. J Am Chem Soc 2011, 133 (11), 3776-3779.

Lippert, A. R.; Van de Bittner, G. C.; Chang, C. J., Boronate oxidation as a bioorthogonal reaction approach for studying the chemistry of hydrogen peroxide in living systems. Accounts of chemical research 2011, 44 (9), 793-804.

Lisanti, M. P.; Martinez-Outschoorn, U. E.; Lin, Z.; Pavlides, S.; Whitaker-Menezes, D.; Pestell, R. G.; Howell, A.; Sotgia, F., Hydrogen peroxide fuels aging, inflammation, cancer metabolism and metastasis: the seed and soil also needs "fertilizer". Cell Cycle 2011, 10 (15), 2440-2449.

Liu, C.; Cao, Z.; Wang, Z.; Jia, P.; Liu, J.; Wang, Z.; Han, B.; Huang, X.; Li, X.; Zhu, B.; Zhang, X., A highly sensitive and reductant-resistant fluorescent chemodosimeter for the rapid detection of nitroxyl. Sensors and Actuators B: Chemical 2015, 220, 727-733.

Mittal, M.; Siddiqui, M. R.; Tran, K.; Reddy, S. P.; Malik, A. B., Reactive Oxygen Species in Inflammation and Tissue Injury. Antioxidants & Redox Signaling 2013, 20 (7), 1126-1167.

Nonaka, H.; Hata, R.; Doura, T.; Nishihara, T.; Kumagai, K.; Akakabe, M.; Tsuda, M.; Ichikawa, K.; Sando, S., A platform for designing hyperpolarized magnetic resonance chemical probes. Nature Communications 2013, 4, 2411.

Park, H., Chen, J., Dimitrov, I.E., Park, J.M. and Wang, Q., 2022. Design and characterization of hyperpolarized 15N-BBCP as a H2O2-sensing probe. ACS sensors, 7(10), pp. 2928-2933. Publication Date:Oct. 18, 2022.

Parvez, S.; Long, M. J. C.; Poganik, J. R.; Aye, Y., Redox Signaling by Reactive Electrophiles and Oxidants. Chemical Reviews 2018, 118 (18), 8798-8888.

Peng, T.; Wong, N.-K.; Chen, X.; Chan, Y.-K.; Ho, D. H.-H.; Sun, Z.; Hu, J. J.; Shen, J.; El-Nezami, H.; Yang, D., Molecular imaging of peroxynitrite with hkgreen-4 in live cells and tissues. J Am Chem Soc 2014, 136 (33), 11728-11734.

Quin C., Robertson L., McQuaker S.J., Price N.C., Brand M.D., Hartley R.C. Caged mitochondrial uncouplers that are released in response to hydrogen peroxide. Tetrahedron. 2010, 66, 2384-2389.

Reth, M., Hydrogen peroxide as second messenger in lymphocyte activation. Nature Immunology 2002, 3 (12), 1129-1134.

Rhee, S. G., H2O2, a Necessary Evil for Cell Signaling. Science 2006, 312 (5782), 1882.

Schieber, M.; Chandel, N. S., ROS function in redox signaling and oxidative stress. Curr Biol 2014, 24 (10), R453-R462.

Sikora, A.; Zielonka, J.; Lopez, M.; Joseph, J.; Kalyanaraman, B., Direct oxidation of boronates by peroxynitrite: Mechanism and implications in fluorescence imaging of peroxynitrite. Free Radical Biology and Medicine 2009, 47 (10), 1401-1407.

Stadtman, E. R.; Levine, R. L., Protein Oxidation. Annals of the New York Academy of Sciences 2000, 899 (1), 191-208.

Szatrowski, T. P.; Nathan, C. F., Production of Large Amounts of Hydrogen Peroxide by Human Tumor Cells. Cancer Research 1991, 51 (3), 794.

Van Der Vliet, A.; Janssen-Heininger, Y. M. W., Hydrogen peroxide as a damage signal in tissue injury and inflammation: murderer, mediator, or messenger? J Cell Biochem 2014, 115 (3), 427-435.

Veal, E. A.; Day, A. M.; Morgan, B. A., Hydrogen Peroxide Sensing and Signaling. Molecular Cell 2007, 26 (1), 1-14.

Wang, Z. J.; Ohliger, M. A.; Larson, P. E. Z.; Gordon, J. W.; Bok, R. A.; Slater, J.; Villanueva-Meyer, J. E.; Hess, C. P.; Kurhanewicz, J.; Vigneron, D. B., Hyperpolarized 13C MRI: State of the Art and Future Directions. Radiology 2019, 291 (2), 273-284.

Wibowo, A.; Park, J. M.; Liu, S.-C.; Khosla, C.; Spielman, D. M., Real-Time in Vivo Detection of H2O2 Using Hyperpolarized 13C-Thiourea. ACS Chemical Biology 2017, 12 (7), 1737-1742.

Xu, J., Zhang, Y., Yu, H., Gao, X. and Shao, S., 2016. Mitochondria-targeted fluorescent probe for imaging hydrogen peroxide in living cells. Analytical chemistry, 88(2), pp. 1455-1461.

Yang, J.; Yang, J.; Liang, S. H.; Xu, Y.; Moore, A.; Ran, C., Imaging hydrogen peroxide in Alzheimer's disease via cascade signal amplification. Scientific Reports 2016, 6 (1), 35613.

Zheng, D.-J.; Yang, Y.-S.; Zhu, H.-L., Recent progress in the development of small-molecule fluorescent probes for the detection of hydrogen peroxide. TrAC Trends in Analytical Chemistry 2019, 118, 625-651.

Zhuang, M.; Ding, C.; Zhu, A.; Tian, Y., Ratiometric fluorescence probe for monitoring hydroxyl radical in live cells based on gold nanoclusters. Analytical Chemistry 2014, 86 (3), 1829-1836.

Zielonka, J.; Sikora, A.; Hardy, M.; Joseph, J.; Dranka, B. P.; Kalyanaraman, B., Boronate Probes as Diagnostic Tools for Real Time Monitoring of Peroxynitrite and Hydroperoxides. Chemical Research in Toxicology 2012, 25 (9), 1793-1799.

\* cited by examiner

COMPOSITIONS COMPRISING HYPERPOLARIZED PROBES FOR $H_2O_2$ SENSING AND METHODS OF USING SAME

CROSS-REFERENCE TO RELATED APPLICATIONS

The present application claims priority to U.S. Provisional Patent Application No. 63/188,797, filed May 14, 2021, the content of which is hereby incorporated by reference in its entirety.

STATEMENT REGARDING FEDERALLY SPONSORED RESEARCH

This invention was made with government support under Federal Grant no. 1R21EB024824 awarded by National Institutes of Health (NIH). The Federal Government has certain rights to this invention.

BACKGROUND OF THE INVENTION

Reactive oxygen species (ROS) are essential cellular metabolites and have been implicated in many diseases including cancer, inflammation, and cardiovascular and neurodegenerative disorders. Among various ROS metabolites, hydrogen peroxide ($H_2O_2$) exists in the highest concentration ($10^{-7}$-$10^{-8}$ M range) and has high stability in physiological conditions. In a healthy system, the production of oxidative species is balanced with an innate antioxidant defense system. However, a disturbance in the redox balance leads to the accumulation of $H_2O_2$, which causes oxidative stress and oxidative damage to biomolecules. Therefore, elevated $H_2O_2$ levels have been a hallmark for various diseases, including cancer, inflammation, and neurodegenerative disorders. The broad actions of $H_2O_2$ in pathophysiology highlight the importance of imaging biological concentration and distribution of $H_2O_2$ for diagnostic and therapeutic applications. Accordingly, practical and efficient sensing probes of oxidative stress applicable for preclinical and clinical models are in high demand.

Development of several optical imaging probes selective for $H_2O_2$ has been reported. Yet, investigation of dynamic $H_2O_2$ activities with high spatial and temporal resolution remains a challenge. Hyperpolarized magnetic resonance spectroscopic imaging (HP-MRSI) is a particularly suited technology for non-invasive detection of the introduced imaging agent and its metabolic products in real-time via reaction-based chemical-shift imaging. HP-MRSI has been established to be a clinically relevant imaging platform, with several hyperpolarized probes successfully applied to investigate metabolism in vivo. Thus, hyperpolarized probes have great potential to image oxidative stress with high spatiotemporal resolution and quantitative analysis. Notably, hyperpolarized $^{13}$C-thiourea ($^{13}$C-TU) and [1-$^{13}$C]-benzoylformic acid ($^{13}$C-BFA) have been demonstrated as HP $H_2O_2$ sensing probes. However, the $^{13}$C centers have short spin-lattice relaxation time ($T_1$) in tens of seconds. Additionally, $^{15}$N-trimethylphenylammonium ($^{15}$N-TMPA) probe has been reported with a long $T_1$ value of over 400 s, but the oxidative reaction afforded a small chemical shift (~1.5 ppm).

Despite the importance of $H_2O_2$ in pathophysiological states, there is a lack of suitable molecular probes for real-time imaging of $H_2O_2$ in vivo as existing probes have poor imaging properties. Thus, there remain a need for effective molecular probes for non-invasive, diagnostic, and therapeutic imaging for preclinical or clinical models of oxidative stress.

SUMMARY

The present disclosure generally relates to molecular probes for real-time imaging of reactive species (e.g., reactive oxygen species). In particular, the present disclosure relates to 15N molecular probes for magnetic resonance imaging of hydrogen peroxide.

In one aspect, the present disclosure provides a compound of Formula (I), or a salt thereof,

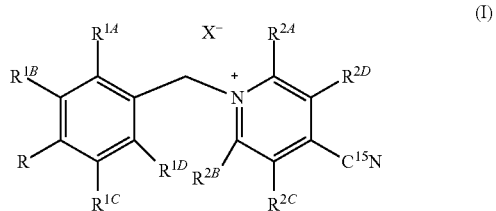

wherein
$R^{1A}$, $R^{1B}$, $R^{1C}$, $R^{1D}$, $R^{2A}$, $R^{2B}$, $R^{2C}$, and $R^{2D}$ are each independently H, CHO, COOH, $SO_3H$, CN, $NO_2$, or $NR^xR^y$;
R is a sensing moiety;
$R^x$ and $R^y$ are each independently H or $C_{1-4}$ alkyl; and
X is a counterion.
In some embodiments, the compound is

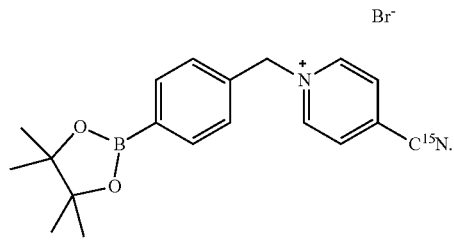

In another aspect, the present disclosure also provides an imaging composition comprising an effective amount of a compound as described herein, or a salt thereof, and at least one additional agent. In some embodiments, the at least one additional agent comprises a polarizing agent.

In another aspect, the present disclosure also provides a pharmaceutical composition comprising an effective amount of a compound as described herein, or a pharmaceutically acceptable salt thereof, and a pharmaceutically acceptable carrier.

In another aspect, the present disclosure also provides a method of analyzing a reactive species in a sample, the method comprising:
  contacting the sample with an effective amount of a compound as described herein, or a salt thereof, thereby the reactive species reacts with the compound to produce a product comprising $^{15}$N; and
  detecting the compound and/or the product, thereby detecting the reactive species in the sample.
In some embodiments, the present method further comprises imaging the compound or and/or the product. For example, the imaging may comprise magnetic resonance imaging (MRI) or magnetic resonance spectroscopic imaging (MRSI). In some embodiments, the reactive species is a reactive oxygen species, such as hydrogen peroxide.

In another aspect, the present disclosure also provides a method of imaging a reactive oxygen species in a sample, comprising:
contacting the sample with an effective amount of a compound as described herein, or a salt thereof, thereby the reactive oxygen species reacts with the compound to produce a product comprising $^{15}N$; and
imaging the compound or and/or the product using magnetic resonance imaging (MRI) or magnetic resonance spectroscopic imaging (MRSI).

In yet another aspect, the present disclosure also provides a method of diagnosing a disease associated with a reactive species in a subject, the method comprising:
administering an effective amount of a compound of claim 1, or a salt thereof, to the subject, thereby the reactive species, if present, reacts with the compound to produce a product comprising $^{15}N$;
detecting the compound and/or the product, thereby determining an amount the reactive species in the subject; and
determining a status of the disease according to the amount the reactive species in the subject.

In some embodiments, the disease is associated with elevated level of hydrogen peroxide. For example, the disease may be cancer, inflammatory disease, aging, cardiovascular disease, diabetes, neurodegenerative disease, stroke, tissue injury, acute lung injury (ALI), chronic lung allograft dysfunction, oxidative stress-induced inflammation within lungs, tissue inflammation, asthma, psoriasis, rheumatoid arthritis, systemic lupus erythematosus (SLE).

BRIEF DESCRIPTION OF THE DRAWINGS

FIG. 5A shows UV/Vis absorption spectra of 50 μM probe reaction with 5 mM (100 equiv) of $H_2O_2$. FIG. 5B shows time-dependent change in $Ab_{310}$ plotted against time.

FIG. 13A shows in vitro time series of hyperpolarized $^{15}N$-BBCP spectra. FIG. 13B shows in vivo observation of hyperpolarized $^{15}N$-BBCP spectra acquired from a rat abdomen at 3 T (insert: temporal changes of $^{15}N$-BBCP peak at 194.8 ppm). FIG. 13C shows in vitro time series of hyperpolarized $^{15}N$-CP at 3 T. FIG. 13D shows in vitro time series and time courses of hyperpolarized $^{15}N$-BBCP and products, observed after mixing with $H_2O_2$ (data for $^{15}N$-BBCP, $^{15}N$-HBCP, $^{15}N$-CP). FIG. 13E shows in vivo reaction-based detection of $H_2O_2$ via $^{15}N$-HBCP production from hyperpolarized $^{15}N$-BBCP.

DETAILED DESCRIPTION OF THE INVENTION

Figure 1A:
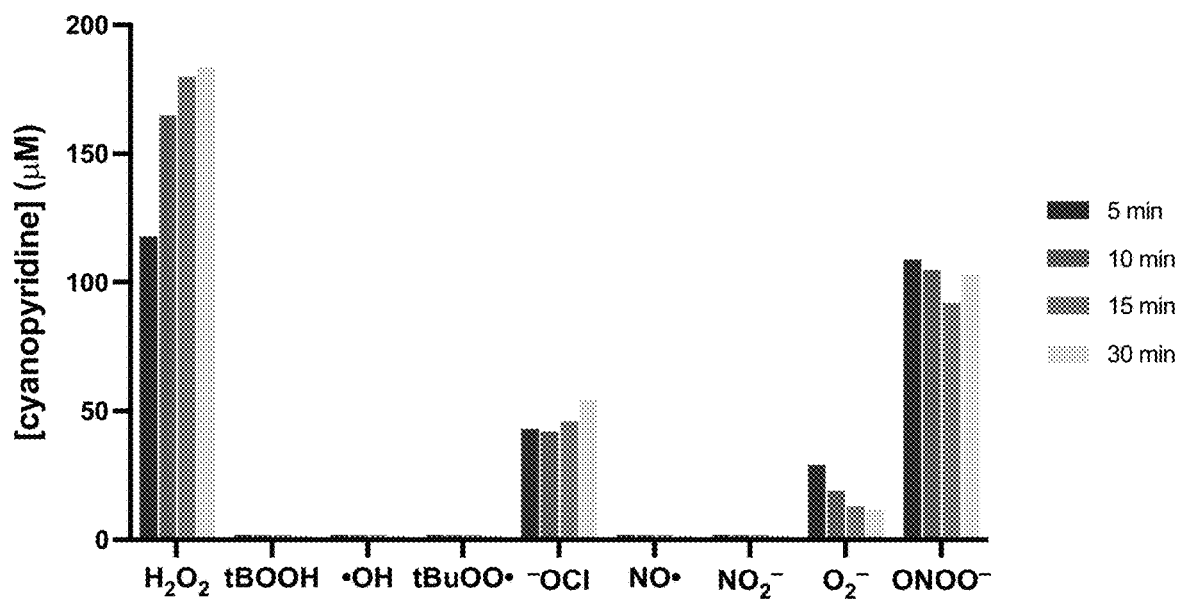
FIG. 1A shows response of BBCP (200 μM) with various ROS/RNS (2 mM) in PBS (pH 7.4). Concentration of 4-cyanopyridine measured by LC/MS after 5, 10, 15, and 30 min of reaction. Abbreviations: $H_2O_2$=hydrogen peroxide; tBuOOH=tert-butyl hydroperoxide; .OH=hydroxyl radical; tBuOO.=tert-butyl hydroxyl radical; $OCl^-$=hypochlorite; NO.=nitric oxide; $NO_2^-$=nitrite; $O_2^-$=superoxide; $ONOO^-$=peroxynitrite.

The present disclosure provides $^{15}N$-labeled molecular probes that can be used for in vivo detection of $H_2O_2$, including quantitative $^{15}N$ magnetic resonance imaging of $H_2O_2$ with high spatiotemporal resolution. The present non-endogenous $^{15}N$-probes may achieve the desired molecular reactivity, imaging capabilities, and physicochemical and biological properties. In particular, the probe and its reaction product may have a distinguishable chemical shift difference. A wide chemical shift range of $^{15}N$ nuclei may be favorable for high detection accuracy and an extended scope of chemical complexity. Further, the $^{15}N$-center in the molecular probe may possess long $T_1$ values in the order of minutes to afford a sufficient imaging window. In addition, the present probes may meet biocompatibility requirements such as aqueous solubility, stability, and cytotoxicity, as well as possess high reaction selectivity and kinetics. In particular embodiments, $^{15}$N-boronobenzyl-4-cyanopyridinium ($^{15}$N-BBCP) is provided as a sensitive and selective H$_2$O$_2$ sensing probe for HP-MSRI. Remarkably, the $^{15}$N-BBCP probe demonstrated extensive polarization lifetime and superior chemical shift differences that allow high imaging sensitivity compared to the previous H$_2$O$_2$ sensing probes.

Definitions

The present disclosure has been described in terms of one or more preferred embodiments, and it should be appreciated that many equivalents, alternatives, variations, and modifications, aside from those expressly stated, are possible and within the scope of the invention. Before the present invention is described, it is understood that this disclosure is not limited to the particular methodology, protocols, and reagents described, as these may vary. It is also to be understood that the terminology used herein is for the purpose of describing particular embodiments only, and is not intended to limit the scope of the present invention which will be limited only by the appended claims.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference for the purpose of describing and disclosing the chemicals, cell lines, vectors, animals, instruments, statistical analysis and methodologies which are reported in the publications which might be used in connection with the invention. Nothing herein is to be construed as an admission that the invention is not entitled to antedate such disclosure by virtue of prior. invention The terms "comprise(s)," "include(s)," "having," "has," "can," "may," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5$^{th}$ Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987; the entire contents of each of which are incorporated herein by reference.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "compound" as used herein, is intended to include any solvates, hydrates, and polymorphs of any of the probes of the present disclosure.

As used herein, the term "solvate" means a compound which further includes a stoichiometric or non-stoichiometric amount of solvent (e.g., water, acetone, ethanol, methanol, dichloromethane, 2-propanol, or the like) bound by non-covalent intermolecular forces.

As used herein, the term "polymorph" means solid crystalline forms of a compound or complex thereof which may be characterized by physical means such as, for instance, X-ray powder diffraction patterns or infrared spectroscopy. Different polymorphs of the same compound can exhibit different physical, chemical and/or spectroscopic properties. Different physical properties include, but are not limited to stability (e.g., to heat, light or moisture), compressibility and density (important in formulation and product manufacturing), hygroscopicity, solubility, and dissolution rates and solubility (which can affect bioavailability). Differences in stability can result from changes in chemical reactivity (e.g., differential oxidation, such that a dosage form discolors more rapidly when comprised of one polymorph than when comprised of another polymorph) or mechanical characteristics (e.g., tablets crumble on storage as a kinetically favored polymorph converts to thermodynamically more stable polymorph) or both (e.g., tablets of one polymorph are more susceptible to breakdown at high humidity). Different physical properties of polymorphs can affect their processing. For example, one polymorph might be more likely to form solvates or might be more difficult to filter or wash free of impurities than another due to the shape or size distribution of particles of it.

The compounds of the present disclosure may contain one or more asymmetric carbon atoms. As such, a compound of this invention can exist as the individual "stereoisomers" (enantiomers or diastereomers) as well a mixture of stereoisomers. Accordingly, a compound of the present invention will include not only a stereoisomeric mixture, but also individual respective stereoisomers substantially free from one another stereoisomers. The term "substantially free" as used herein means less than 25% of other stereoisomers, preferably less than 10% of other stereoisomers, more preferably less than 5% of other stereoisomers and most preferably less than 2% of other stereoisomers, are present. Methods of obtaining or synthesizing diastereomers are well known in the art and may be applied as practicable to final compounds or to starting material or intermediates. Other embodiments are those wherein the compound is an isolated compound. It is well known in the art how to prepare optically active forms, such as by resolution of racemic forms or by synthesis from optically active starting materials. All processes used to prepare compounds of the present invention and intermediates made therein are considered to be part of the present invention. All tautomers of shown or described compounds are also considered to be part of the present disclosure.

Compounds

In aspect, the present disclosure provides a compound of Formula (I), or a salt thereof, $$\text{(I)}$$

wherein
$R^{1A}$, $R^{1B}$, $R^{1C}$, $R^{1D}$, $R^{2A}$, $R^{2B}$, $R^{2C}$, and $R^{2D}$ are each independently H, CHO, COOH, $SO_3H$, CN, $NO_2$, or $NR^xR^y$;
R is a sensing moiety;
$R^x$ and $R^y$ are each independently H or $C_{1-4}$ alkyl; and
X is a counterion.

A "sensing moiety" in the present compounds refers to a substituent group capable of reacting with a reactive species, such as a reactive oxygen species, a reactive nitrogen species, or reactive sulfur species. A sensing reaction between the sensing moiety and the reactive species may result in the removal of the sensing moiety from the remainder of the parent compound. For example, the sensing reaction may result in hydrolysis, oxidation, and/or elimination of the sensing moiety, thereby releasing the remainder of the parent compound as a product of the reaction. Following the sensing reaction, the sensing moiety may be replaced, entirely or partially, by H or OH in the product compound. For example, a boronic ester group (e.g., $(R'O)_2B$—) as a sensing moiety may be oxidized by hydrogen peroxide (as a reactive oxygen species) to produce a hydroxyl group (HO—) and the product compound is an alcohol corresponding to the parent compound.

Examples of reactive oxygen species (ROS) include, but are not limited to, peroxides, superoxides, hydroxyl radical (.OH), singlet oxygen, and alpha-oxygen. In some embodiments, the ROS is a peroxide, such as hydrogen peroxide ($H_2O_2$). Examples of reactive nitrogen species (RNS) include, but are not limited to, peroxynitrite ($ONOO^-$), nitrogen dioxide (.$NO_2$), dinitrogen trioxide ($N_2O_3$), and nitroxyl (HNO). In some embodiments, the RNS is peroxynitrite or nitroxyl (HNO). Examples of reactive sulfur species include, but are not limited to, hydrogen sulfide ($H_2S$), hydrogensulfite ($HSO_3^-$), sulfhydryl radical (.SH), persulfides, polysulfides, and thiosulfate. In some embodiments, the reactive sulfur species is $H_2S$.

In some embodiments, R is $(R'O)_2B$—,

-continued wherein
$R^t$ is $C_{1-4}$ alkyl;
R' and R" at each occurrence are independently H or $C_{1-4}$ alkyl;
$R^3$ is OH, $OCH_3$, or $NH_2$; and
n is 2 or 3.
In some embodiments, R is In some embodiments, R' and R" are both H or $C_{1-4}$ alkyl. In some embodiments, R' and R" are different. In some embodiments, R' and R" are identical. In some embodiments, R' and R" are both H or methyl. In some embodiments, n is 2. For example R may be In some embodiments, R is In some embodiments, R is $R^3$ is OH, $OCH_3$, or $NH_2$.

In some embodiments, R is

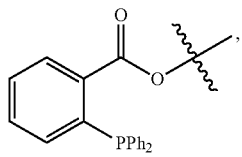

In some embodiments, R is

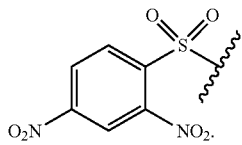 [SMILES: *S(=O)(=O)c1ccc([N+](=O)[O-])cc1[N+](=O)[O-]]

In some embodiments, $R^{1A}$, $R^{1B}$, $R^{1C}$ and $R^{1D}$ are H; and at least one of $R^{2A}$, $R^{2B}$, $R^{2C}$, and $R^{2D}$ is CHO, COOH, $SO_3H$, CN, $NO_2$, or $NR^xR^y$. In some embodiments, at least one of $R^{1A}$, $R^{1B}$, $R^{1C}$ and $R^{1D}$ is CHO, COOH, $SO_3H$, CN, $NO_2$, or $NR^xR^y$; and $R^{2A}$, $R^{2B}$, $R^{2C}$, and $R^{2D}$ are H. In some embodiments, $R^{1A}$, $R^{1B}$, $R^{1C}$, $R^{1D}$, $R^{2A}$, $R^{2B}$, $R^{2C}$, and $R^{2D}$ are H.

X may be any suitable negatively charged counterion known in the art. In some embodiments, X is halide, sulfonate, sulfate, phosphonate, phosphate, acetate, oxalate, fumarate, tartrate, or lactate. In some embodiments, X is Cl, Br, I, or $CH_3SO_3$. In some embodiments, X is Br.

In some embodiments, the compound is

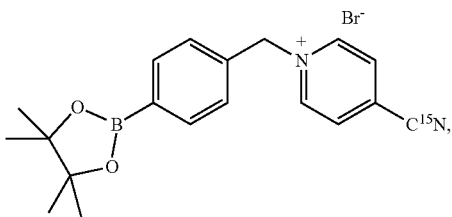

or a salt thereof.

The salt may be, for example, a pharmaceutically acceptable salt. The term "pharmaceutically acceptable salt" refers to salts derived from a variety of organic and inorganic counter ions known in the art. Pharmaceutically acceptable acid addition salts can be formed with inorganic acids and organic acids. Inorganic acids from which salts can be derived include, for example, hydrochloric acid, hydrobromic acid, sulfuric acid, nitric acid and phosphoric acid. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid and salicylic acid. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese and aluminum. Organic bases from which salts can be derived include, for example, primary, secondary, and tertiary amines, substituted amines including naturally occurring substituted amines, cyclic amines and basic ion exchange resins. Specific examples include isopropylamine, trimethylamine, diethylamine, triethylamine, tripropylamine, and ethanolamine. In some embodiments, the pharmaceutically acceptable base addition salt is chosen from ammonium, potassium, sodium, calcium, and magnesium salts.

Compositions

In another aspect, provided is an imaging composition comprising an effective amount of a compound as described herein, or a salt thereof, and at least one additional agent.

The additional agents of the imaging composition may be, for example, a carrier, an excipient, a solvent, a pH buffer, a stabilizer, a contrast agent, a polarizing agent, a therapeutic agent, a diagnostic agent, or a combination thereof. In some embodiments, the additional agents may provide a system for intracellular delivery, improve the transport of the present compound to its site of action, improve the stability of the present compound in vivo, prolong the residence time of the present compound at its site of action by reducing clearance, decrease toxicity of the present compound, improve taste of the imaging composition; or improve shelf life of the imaging composition.

In some embodiments, the at least one additional agent includes a polarizing agent. A polarizing agent may be any agent suitable for performing ex vivo polarization of an magnetic imaging compound as described herein. Suitable polarizing agents include known agents used for magnetic resonance studies. Examples of polarizing agents include, but are not limited to, hydroxyethyl tetrathiatriarylmethyl radical (Ox063), pentacene, 6,13-diazapentacene (DAP), and 5,12-diazatetracene (DAT), 1,3-bisdiphenylene-2-phenylallyl (BDPA), and derivatives thereof. In some embodiments, the polarizing agent comprises Ox063 or a derivative thereof.

In another aspect, provided is pharmaceutical composition comprising an effective amount of a compound as described herein, or a pharmaceutically acceptable salt thereof, and a pharmaceutically acceptable carrier.

As used herein, the term "effective amount" refers to amounts of a compound or agent that is sufficient for imaging, diagnostic, or therapeutic applications. A "therapeutically effective amount" refers to an amount effective, at dosages and for periods of time necessary, to achieve the desired therapeutic result, such as beneficial or desirable biological and/or clinical results. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of the present pharmaceutical composition are outweighed by the therapeutically beneficial effects.

The term "pharmaceutically acceptable," as used herein, refers to any carrier, excipient, or ingredient, which is useful in the preparation of a pharmaceutical composition, which is generally safe, non-toxic and neither biologically nor otherwise undesirable, and which is acceptable for veterinary use as well as for human application.

A carrier, such as a pharmaceutically acceptable carrier, may be a non-toxic, inert solid, semi-solid or liquid filler, diluent, encapsulating material or formulation auxiliary of any type. Suitable carriers include, but are not limited to, diluents, preservatives, solubilizers, emulsifiers, liposomes, nanoparticles and adjuvants. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Compositions of the present disclosure may include liquids, lyophilized, or otherwise dried formulations and may include diluents of various buffer content (e.g., Tris-HCl, acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the polypeptide, complexation with metal ions, or incorporation of the material into or onto particulate preparations of polymeric compounds such as polylactic acid, polyglycolic acid, hydrogels, etc., or onto liposomes, microemulsions, micelles, bilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils).

The compositions can be sterilized by conventional, well-known sterilization techniques. The compositions may contain pharmaceutically acceptable additional substances as required to approximate physiological conditions such as a pH adjusting and buffering agent, toxicity adjusting agents, such as, sodium acetate, sodium chloride, potassium chloride, calcium chloride, sodium lactate, and the like.

The present compositions may be formulated for administration by, for example, solid dosing, eyedrop, in a topical oil-based formulation, injection, inhalation (either through the mouth or the nose), implants, oral, buccal, parenteral, or rectal administration. Techniques and formulations may generally be found in "Remington's Pharmaceutical Sciences", (Meade Publishing Co., Easton, Pa.). Therapeutic compositions typically are sterile and stable under the conditions of manufacture and storage.

The route by which the present composition is administered and the form of the composition may dictate the type of carrier to be used. The composition may be administered, for example, by oral, rectal, sublingual, parenteral, or topical administration. Parenteral administration may include, for example, intramuscular, intraperitoneal, intravenous, and transdermal administration. The composition may be in a variety of forms, suitable, for example, for systemic administration (e.g., oral, rectal, sublingual, buccal, implants, or parenteral) or topical administration (e.g., dermal, pulmonary, nasal, aural, ocular, liposome delivery systems, or iontophoresis).

Carriers for systemic administration may include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmelose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of active agent and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, for example, at least 5% and more particularly from about 25% to about 50% of actives. The oral dosage compositions may include about 50% to about 95% of carriers, such as from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmelose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound, and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not limited for the present compositions.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT coatings (available from Rohm & Haas G.M.B.H. of Darmstadt, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the present compounds include sublingual, buccal and nasal dosage forms. Such compositions may include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

In some embodiments, the present composition is administered by a route suitable for performing magnetic resonance (MR) imaging in a recipient, including but not limited to oral, parenteral (including subcutaneous, intradermal, intramuscular, intravenous and intraarticular), rectal administration, as well as administration by inhalation. The composition may conveniently be presented in unit dosage form and may be prepared by any of the methods well known in the art of pharmacy. The preparation of the composition may include mixing a compound of the present disclosure ("active ingredient") with suitable carrier or diluent which may constitute one or more accessory ingredients. For example, the present compositions may be prepared by uniformly and intimately bringing into association the active ingredient with liquid carriers or finely divided solid carriers or both and then, if necessary, shaping the product into the desired formulation. Generally accepted formulations are well known in the art (e.g., Remington: The Science and Practice of Pharmacy, A. R. Gennaro, ed. (1995), the entire disclosure of which is incorporated herein by reference.)

The present imaging and pharmaceutical compositions may be conveniently presented in unit dosage form and prepared by any of the methods well known in the art of pharmacy. Exemplary unit dosage formulations are those containing an effective dose, or an appropriate fraction thereof, of the active ingredient, or a pharmaceutically acceptable salt thereof. The magnitude of a diagnostic dose typically varies with the nature of the redox system to be queried and the route of administration. The dose in the formulation, and perhaps the dose frequency, will also vary according to the age, body weight and response of the individual patient. The total dose (in single or divided doses) may range from about 1 mg to about 7000 mg, such as about 1 mg to about 100 mg, from about 10 mg to about 100 mg, or from about 20 mg to about 100 mg.

In various embodiments, the present disclosure provides compositions in which the hyperpolarized MR imaging probe is present in a concentration of about 0.1 mM to about 10 M, e.g., about 10 mM to about 10 M, about 10 mM to about 1 M, or about 50 mM to about 500 mM. For various embodiments in which bolus injection is utilized, the concentration may be from about 0.1 mM to about 10 M, e.g., from about 0.2 mM to about 10 M, from about 0.5 mM to about 1 M, from about 1.0 mM to about 500 mM, or about 10 mM to about 300 mM.

Children, patients over 65 years old, and those with impaired renal or hepatic function, may initially receive low doses, and the dosage may be titrated based on individual responses and/or blood levels. It may be necessary to use dosages outside these ranges in some cases, as will be apparent to those in the art. The administration of the present compositions may be interrupted, adjusted, or terminated according to individual patient's response and the determination of the clinician or treating physician.

In some embodiments, compositions suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste. The pill and capsule formulations are convenient vehicles for preparation and storage of a unit dosage formulation. When the compound is in a solid form in the pharmaceutical formulation, it is generally dissolved in a pharmaceutically acceptable diluent prior to polarization and use.

In some embodiments, compositions suitable for parenteral administration include aqueous and non-aqueous sterile injection solutions which may contain anti-oxidants, buffers, bacteriostats and solutes which render the composition isotonic with the blood of the intended recipient. Compositions suitable for parenteral administration also include aqueous and non-aqueous sterile suspensions, which may include suspending agents and thickening agents. The compositions may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described. Compositions for rectal administration may be presented as a suppository with the usual carriers such as cocoa butter or polyethylene glycol. Compositions for topical administration in the mouth, for example, buccally or sublingually, include lozenges comprising the active ingredient in a flavored basis such as sucrose and acacia or tragacanth, and pastilles comprising the active ingredient in a basis such as gelatin and glycerin or sucrose and acacia.

The pharmaceutically acceptable diluent may take a wide variety of forms, depending on the route desired for administration, for example, oral or parenteral (including intravenous). In preparing the composition for oral dosage form, any of the usual pharmaceutical media may be employed, such as, water, glycols, oils, alcohols, flavoring agents, preservatives, and coloring agents in the case of oral liquid preparation, including suspension, elixirs and solutions. Carriers such as starches, sugars, microcrystalline cellulose, diluents, granulating agents, lubricants, binders and disintegrating agents may be used in the case of oral solid preparations such as powders, capsules and caplets. Exemplary solid oral preparations are tablets or capsules, because of their ease of administration. If desired, tablets may be coated by standard aqueous or nonaqueous techniques. Oral and parenteral sustained release dosage forms may also be used.

In some embodiments, the imaging or pharmaceutical composition is a unit dosage formulation. For example, a compound as described herein may be present in an amount needed to administer sufficient compound to a subject to perform a desired imaging experiment, or series of imaging experiments. In an exemplary unit dosage formulation, the compound may be present in an amount sufficient to provide a dosage of from about 0.5 mg/kg to about 50 mg/kg, e.g., from about 1 mg/kg to about 25 mg/kg. In some embodiments, the compound is present in the dosage formulation in an amount sufficient to provide a dosage of from about 0.5 mg/kg to about 5 mg/kg, e.g., from about 0.7 mg/kg or about 1 mg/kg.

In some embodiments, for in vivo use, a hyperpolarized solid MR imaging probe is dissolved in a liquid administrable media (e.g., water or saline), administered to a subject and an MR image recorded. Thus, solid MR imaging agents are preferably rapidly soluble (e.g., water soluble) to assist in formulating administrable media. In some embodiments, the MR imaging probe dissolves in a physiologically tolerable carrier (e.g., water or saline) to a concentration of at least 1 mM. In another embodiment, the compound of the present disclosure is hyperpolarized in the solid state by, for example, a dynamic nuclear polarization technique, and the hyperpolarized compound is subsequently formulated for administration by the desired route.

In some embodiments, the hyperpolarized compound is initially dissolved at a concentration higher than the concentration at which it will be administered. The concentrated hyperpolarized compound may be diluted to a concentration appropriate for administering to a subject. In some embodiments, the compound is dissolved at an administrable concentration and the solution may be hyperpolarized.

In some embodiments, the compound of the present disclosure is formulated with another agent, such as another MR sensitive compound (e.g., paramagnets, other hyperpolarized compounds) and/or other diagnostic agents. In some embodiments, the compositions of the present disclosure further include a therapeutic agent and/or a diagnostic agent.

Methods of Use

In another aspect, the present disclosure provides a method of analyzing a reactive species in a sample, the method comprising:

contacting the sample with an effective amount of a compound as described herein, or a salt thereof, thereby the reactive species reacts with the compound to produce a product comprising $^{15}N$; and detecting the compound and/or the product, thereby detecting the reactive species in the sample.

The sample may be a biological sample, an environmental sample, a forensic sample, or an industrial sample. The term "biological sample" as used herein includes, but is not limited to, a sample containing tissues, cells, and/or biological fluids isolated from a subject. Examples of biological samples include, but are not limited to, tissues, cells, biopsies, blood, lymph, serum, plasma, urine, saliva, mucus and tears. In one embodiment, the biological sample is a biopsy (such as a tumor biopsy). A biological sample may be obtained directly from a subject (e.g., by blood or tissue sampling) or from a third party (e.g., received from an intermediary, such as a healthcare provider or lab technician). The sample may be a disease sample, such as a sample derived from a human having the disease or an animal model of the disease. The disease may be, for example, cancer, metabolic disease, cardiovascular disease, respiratory disease, infectious disease.

As used herein, the term "subject" and "patient" are used interchangeably herein and refer to both human and non-human animals. Non-human animals include all vertebrates, e.g., mammals and non-mammals, such as nonhuman primates, sheep, dog, cat, horse, cow, chickens, amphibians, reptiles, and the like. The methods and compositions disclosed herein may be used on a sample either in vitro (for example, on isolated cells or tissues) or in vivo in a subject (e.g., living organism, such as a patient).

In some embodiments, the sample is a cell. In some embodiments, the cell is a live cell. The live cell may be, for example, derived from a patient, an animal, or a cell line.

The term "contacting" as used herein, such as "contacting a sample," refers to contacting a sample directly or indirectly in vitro, ex vivo, or in vivo (e.g., within a subject as defined herein). Contacting a sample may include addition of a compound to a sample, or administration the compound to a subject. Contacting may include administration of the compound to a solution, a cell, a tissue, a mammal, a subject, a patient, or a human. For example, contacting a cell with a compound may include adding the compound to a cell culture.

In some embodiments, the compound is detected. The product can be an intermediate or a final product. In some embodiments, the product is detected. In some embodiments, both the compound and the product are detected. For example, the decrease of the compound and/or the increase of the product may indicate occurrence of the reaction and presence (or concentration) of the reactive species in the sample.

In some embodiments, the method further comprises quantitating the reactive species. The quantitation may be carried out using known techniques (e.g., by using standard curve and/or internal standards).

Suitable technologies for detection include, but are not limited to, mass spectrometry and magnetic resonance. In some embodiments, detecting the compound and/or the product comprises detecting the compound and/or the product by magnetic resonance. In some embodiments, the detection is carried out by detecting $^{15}N$ signal (e.g., from the compound and/or the product) using magnetic resonance spectroscopy or imaging (MRS/MRI).

In some embodiments, the method further comprises imaging the compound or and/or the product. The term "imaging" as used herein includes any suitable photographic or video recording of a signal produced by a substance (e.g., a magnetic resonance signal) that is detected in the imaging process. For a hyperpolarized probe, such as a $^{15}N$-labeled compound or product disclosed herein, the imaging may include techniques such as recording a chemical shift of the probe, magnetic resonance imaging (MRI), magnetic resonance spectroscopic imaging (MRSI), or a combination thereof. In addition, nuclear magnetic resonance (NMR) may be used to image non-living samples, such as an aqueous solution with reactive species. The method may also include a hyperpolarization step using known techniques, which enables detection of miniscule concentration of the compound and/or product using MRI, MRSI, or NMR (e.g., hyperpolarized MRI, or HP-MRI). The imaging process may be carried out using any suitable instruments and techniques known in the art.

In some embodiments, the imaging comprises magnetic resonance imaging (MRI) or magnetic resonance spectroscopic imaging (MRSI).

The reactive species may be any species that reacts with the sensing moiety of present compounds. In some embodiments, the reactive species comprises a reactive oxygen species, a reactive nitrogen species, or a combination thereof, as described herein. In some embodiments, the reactive species is a reactive oxygen species. The reactive oxygen species may comprise, for example, hydrogen peroxide. In some embodiments, the reactive species in the sample is hydrogen peroxide.

In some embodiments, the compound is a compound of Formula (I), or a salt thereof, wherein R is

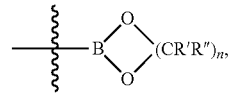

as disclosed herein.

In some embodiments, the compound is

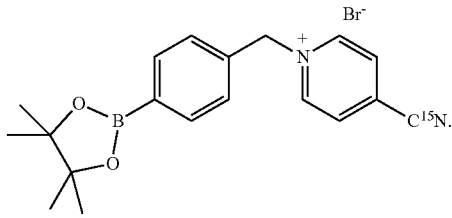

In some embodiments, the product is

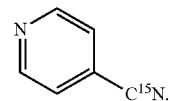

The method as disclosed herein may provide an approach to image the reactive species in the sample (e.g., a cell), which may reveal a profile of the sample being imaged. The profile may include, for example, a reactive species profile, a metabolic profile, and/or a singling profile. The present imaging process may include real time imaging, in which the progress of the reaction between the reactive species and the probe compound may be monitored. The profile of the sample (e.g., a profile as revealed by real time imaging results) may in turn provide important physiological or pharmacological information about the sample.

Accordingly, in another aspect, the present disclosure provides a method of imaging a reactive oxygen species in a sample, comprising:
 contacting the sample with an effective amount of a compound as described herein, or a salt thereof, thereby the reactive oxygen species reacts with the compound to produce a product comprising $^{15}N$; and
 imaging the compound or and/or the product using magnetic resonance imaging (MRI) or magnetic resonance spectroscopic imaging (MRSI).

In yet another aspect, the present disclosure provides a method of diagnosing a disease associated with a reactive species in a subject, the method comprising
 administering an effective amount of a compound as described herein, or a salt thereof, to the subject, thereby the reactive species, if present, reacts with the compound to produce a product comprising $^{15}N$;
 detecting the compound and/or the product, thereby determining an amount the reactive species in the subject; and
 determining a status of the disease according to the amount the reactive species in the subject.

The disease may be characterized by an elevated or decreased level of the reactive species as compared to a normal level of such species in subjects without the disease.

For example, the disease may be characterized by an elevated level of the reactive species that is about 150%, about 200%, about 500%, about 1000%, about 5000%, about 10000% of the normal level. For example, the disease may be characterized by an decreased level of the reactive species that is about 50%, about 20%, about 10%, about 1%, or about 0.1% of the normal level.

In some embodiments, the disease is a disease associated with a reactive oxygen species. The reactive oxygen species may be, for example, hydrogen peroxide.

In some embodiments, the disease is associated with an elevated level of hydrogen peroxide, such as cancer (e.g., lung or breast cancer), inflammatory disease, aging, cardiovascular disease (e.g., atherosclerosis, ischemia), diabetes, neurodegenerative disease (e.g., Alzheimer's disease), stroke, tissue injury, acute lung injury (ALI), chronic lung allograft dysfunction, oxidative stress-induced inflammation within lungs, tissue inflammation, asthma, psoriasis, rheumatoid arthritis, systemic lupus erythematosus (SLE). In some embodiments, the disease is cancer, such as lung cancer or breast cancer.

As disclosed herein, the sample being analyzed or imaged by the present methods may be an in vitro, an ex vivo, or an in vivo sample. For example, the sample can be a cell, a tissue, or an organ from a subject or patient that is analyzed or imaged in vitro or in vivo. Similarly, in the present diagnosis methods, the amount the reactive species in a subject may be determined in a tissue or an organ of the subject, for example, by an in vitro or in vivo detection of the compound and/or the product in the tissue or the organ as described herein.

The amount of the reactive species in a tested subject includes absolute amounts (e.g., concentration in mM) and relative amounts as compared to the normal level of such species in subjects without the disease. For example, the amount the reactive species in a tested subject may be about 20%, about 50%, about 100%, about 200%, about 500%, about 1000%, or about 10000% of the normal level.

The "status" of the disease includes, but is not limited to, no disease, early stage disease, stable disease, progressive stage disease, advanced stage disease. For example, an amount of the reactive species close to (e.g., 90% to 110% relative to) the normal level may indicate no disease. Alternatively, an elevated amount of the reactive species (e.g., at least 200%) relative to the normal level may indicate the presence or manifestation of a disease. A continued deviation (e.g., elevation) of the amount the reactive species from the normal level may indicate a progressive stage of the disease.

In some embodiments, the subject has previously been treated by a therapeutic agent, and the diagnosis method may further comprise determining the efficacy of the therapeutic agent, for example, by comparing the amounts of the reactive species in the subject before and after the treatment.

In certain embodiments, the present disclosure provides in vivo and in vitro methods for querying a sample, a system, or a subject using MR in combination with a hyperpolarized compound of the present disclosure. The method may include administering a hyperpolarized compound of the present disclosure to the sample, the system, or the subject and recording an MR image of a region of the sample, the system, or the subject including the hyperpolarized compound of the present disclosure.

In certain embodiments, the methods according to the present disclosure comprises administering to a subject a detectable amount of a hyperpolarized probe of the present disclosure and acquiring an MR image post-administration. The MR image may include a region in which the hyperpolarized probe is distributed. In some embodiments, the hyperpolarized probe comprises $^{15}$N-BBCP.

In some embodiments, the methods of the present disclosure are carried out within the time that a MR imaging agent (e.g., a compound as described herein) remains significantly polarized. Thus, in various embodiments, once nuclear spin polarization and dissolution has occurred, the administration of the MR imaging agent is effected rapidly and the MR measurement follows shortly thereafter. Accordingly, it is generally preferred that the subject, sample, or system is available and close to the area in which the polarization has been carried out. If this is not possible, the polarized compound of the invention should be transported to the relevant area, preferably at low temperature.

In various embodiments, the administration route for the polarized MR imaging compound is parenteral e.g., by bolus injection, by intravenous, intraarterial or peroral injection. The injection time may be scaled to the $T_1$ of the hyperpolarized compound. For example, an injection time equivalent to 5 $T_1$ or less, 3 $T_1$ or less, $T_1$ or less, or even 0.1 $T_1$ or less may be used.

In some embodiments, a lung and/or another component of the airway of a subject may be imaged by spray, such as aerosol spray.

For in vivo imaging, a formulation (e.g., a substantially isotonic formulation) may be administered at a concentration sufficient to yield a concentration of the MR imaging probe in the imaging zone of from about 1 μM to about 1 M. However, the choice of concentration and dosage may depend upon a range of factors such as toxicity, the organ targeting ability of the MR imaging probe, and the administration route. Suitable concentration for the MR imaging agent may represent a balance between various factors. In some embodiments, the concentration may be about 0.1 mM to about 10 M, such as about 0.2 mM to about 1 M or about 0.5 mM to about 500 mM.

Formulations of use in the methods of the present disclosure suitable for intravenous or intraarterial administration may comprise the MR imaging probe in a concentration of about 10 mM to about 10M, such as about 50 mM to about 500 mM. For bolus injection, the concentration may be about 0.1 mM to about 10 M, such as about 0.2 mM to about 10 M, about 0.5 mM to about 1 M, about 1.0 mM to about 500 mM, or about 10 mM to about 300 mM.

The dosages of the MR imaging probe used in the method of the present disclosure may vary according to the MR imaging probe used, the tissue or organ of interest, and the measuring apparatus. The dosage may be kept as low as possible whilst still achieving a detectable contrast effect. In various embodiments, the dosage is approximately 10% of $LD_{50}$, e.g., in the range of about 1 mg/kg to about 1000 mg/kg, such as about 2 mg/kg to about 500 mg/kg or about 3 mg/kg to about 300 mg/kg. As discussed herein, these amounts may be delivered in single (or unit) or multiple dosages.

In certain embodiments, the present disclosure provides a means of functional MR imaging of a component of a system (e.g., a cell) as provided herein. In some embodiments, the functional imaging detects an activity of a receptor implicated in the system.

In various embodiments, the present disclosure provides systems and methods for determining the amount of a probe of the present disclosure taken up a by a cell or tissue. For example, the amount may be determined by detecting an NMR signal corresponding to a probe of the present disclosure which has been reduced or oxidized by the intracellular conditions (and/or intercellular conditions in a tissue) and evaluating the signal. The evaluation may be qualitative or quantitative. In various embodiments, this method may be used to detect active transport of the probe into a cell.

In some embodiments, the present disclosure provides systems and in vitro methods of probing systems (e.g., redox systems) in organ systems, perfused cell systems and in enzyme systems. These methods may be used to elucidate the mechanism of activity in a particular system and/or in drug discovery and optimization. The method may comprise administering to the system a hyperpolarized compound of the present disclosure and acquiring an MR image of a region of the system containing the hyperpolarized compound of the present disclosure. Example systems of use in the present disclosure include those known in the art, such as those discussed in Keshari et al. (Magnetic Resonance in Medicine, 2010, 63 (2), pp. 322-329).

Aspects of the present disclosure that are described with respect to methods can be utilized in the context of the compositions of matter discussed in this disclosure. Similarly, aspects of the present disclosure that are described with respect to compositions of matter can be utilized in the context of the methods. The present disclosure is more fully understood upon consideration of the following non-limiting examples.

EXAMPLES

General experiment information. Unless otherwise noted, reactions were performed without exclusion of air or moisture. All commercially available reagents and solvents were used as received unless otherwise stated. Analytical thin-layer chromatography (TLC) was performed using aluminum plates pre-coated with 0.25 mm of 230-400 mesh silica gel impregnated with a fluorescent indicator (254 nm). TLC plates were visualized by exposure to ultraviolet light and/or vanillin and/or $KMnO_4$ stains. Organic solutions were concentrated in vacuo using a rotary evaporator. Column chromatography was performed with silica gel (60 Å, standard grade).

Nuclear magnetic resonance spectra were recorded at ambient temperature (unless otherwise stated) on Varian iNova 500 MHz spectrometers. Proton and carbon chemical shifts ($^1H$, $^{13}C$) are quoted in parts per million and referenced to the residual internal $CHCl_3$ ($\delta$ 7.26) or $D_2O$ ($\delta$ 4.79). All values for nitrogen-15 chemical shifts ($\delta_N$) are reported in parts per million and are referenced to an external standard of $^{15}N_2$-urea ($\delta$ 0.0); the reference point is calculated from the ratios of resonance frequencies following IUPAC recommendations. Resonances are described as s (singlet), d (doublet), t (triplet), q (quartet), quint (quintet), and combinations thereof. Coupling constants (J) are given in Hz and rounded to the nearest 0.1.

High resolution mass spectra were recorded by the Mass Spectrometry Facility at the Department of Chemistry at Duke University using an Agilent 6224 TOF LC/MS instrument (denoted by LC/ESI). High resolution m/z values are reported in Daltons, calculated to 4 decimal points from the molecular formula. All found values are within 5 ppm tolerance.

Infrared spectra were recorded on a ThermoScientific Nicolet 6700 FTIR equipped with a diamond ATR. Absorption maxima ($\nu_{max}$) are described as s (strong), m (medium), w (weak), and br (broad) and are quoted in wavenumbers ($cm^{-1}$). Only selected peaks are reported.

Example 1: Chemical Synthesis of $^{15}N$-BBCP as a $H_2O_2$ Sensor

The structural design of $^{15}N$-BBCP comprised of aryl boronate as a $H_2O_2$ sensing unit and $^{15}N$-nitrile as a signaling unit, connected through a pyridinium linkage (Scheme 1). The oxidation of aryl boronic ester/acid may unmask a phenol intermediate (hydroxybenzyl-4-cyanopyridinium, 15N-HBCP), which would undergo a concurrent 1,6-elimination to release $^{15}N$-4-cyanopyridine ($^{15}N$-CP) and quinone methide (QM). Thermal scans of $^{15}N$-BBCP (194.8 ppm) and $^{15}N$-CP (180.9 ppm) using $^{15}N_2$-urea as a reference displayed a chemical shift difference of ~14 ppm between the two species. The two species also showed a large $^{15}N$ chemical shift in NMR ($^{15}N$-BBCP 276 ppm (MeOD), $^{15}N$-4-cyanopyridine 264 ppm (MeOD), $^{15}N$ NMR ~12 ppm). It was envisioned that both $^{15}N$-HBCP and $^{15}N$-CP may be captured as signal readouts in $H_2O_2$ sensing studies. The chemical shift difference between $^{15}N$-BBCP and $^{15}N$-HBCP, however, may be smaller due to the distance of the $^{15}N$-center from the reaction site. The pyridinium linker was highly favorable in our design, as it provided a large chemical shift change when cleaved to pyridine and the positive charge granted high aqueous solubility of the probe.

Scheme 1. Design principle of $^{15}N$-labeled $H_2O_2$ sensing probe.

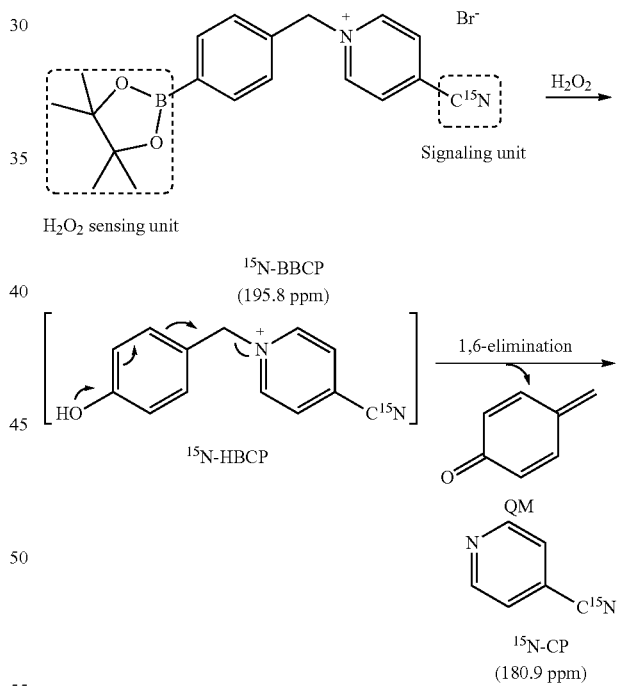

Proposed two-step $H_2O_2$ sensing mechanism of $^{15}N$-BBCP involving boron oxidation followed by 1,6-elimination.
Abbreviations:
$H_2O_2$ = hydrogen peroxide;
BBCP = boronobenzyl-4-cyanopyridinium,
HBCP = hydroxybenzyl-4-cyanopyridinium;
QM = quinone methide;
CP = cyanopyridine.

Here, $^{15}N$-BBCP was synthesized by conjugation of 2 with $^{15}N$-CP (Scheme 2). The isotope-enriched $^{15}N$-CP was facilely synthesized from condensation of $^{15}N$-hydroxylamine hydrochloride and 4-pyridinecarboxaldehyde.

Scheme 2. Synthetic routes to $^{15}$N-CP and $^{15}$N-BBCP.

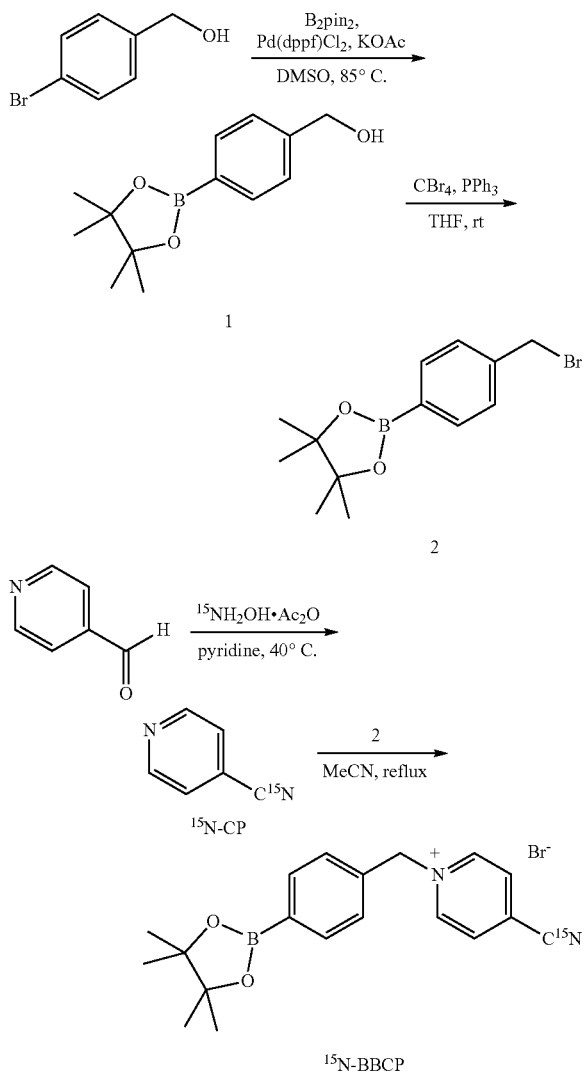

Abbreviations:
B$_2$pin$_2$ = bis(pinacolato)diboron;
Pd(dppf)Cl$_2$ = (1,1'-Bis(diphenylphosphino)ferrocene)palladium(II) dichloride;
KOAc = potassium acetate;
DMSO = dimethyl sulfoxide;
CBr$_4$ = carbon tetrabromide;
PPh$_3$ = triphenylphospine;
THF = tetrahydrofuran;
$^{15}$NH$_2$OH·HCl = 15N-hydroxylamine hydrochloride;
Ac$_2$O = acetic anhydride;
MeCN = acetonitrile.

$^{15}$N-4-cyanopyridine ($^{15}$N-CP)

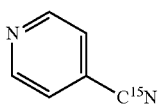

To a dram vial was added 4-pyridinecarboxaldehyde (94 µL, 1.0 mmol, 1.0 equiv) and pyridine (0.5 mL). To the mixture was added $^{15}$NH$_2$OH·HCl (77 mg, 1.1 mmol, 1.1 equiv) and the reaction was heated to 50° C. for 2 h. To the mixture was then added Ac$_2$O (170 µL, 1.8 mmol, 1.8 equiv) and allowed to stir overnight. The reaction was then cooled to room temperature and concentrated in vacuo. The crude mixture was subjected to silica gel chromatography (3% NEt$_3$, 2:3 EtOAc/hexanes) to afford the product as a white solid (71 mg, 67%). $^1$H NMR (500 MHz, CDCl$_3$): δ 8.20 (d, J=6.0 Hz, 2H), 7.4 (d, J=6.0 Hz, 2H); $^3$C NMR (126 MHz, CDCl$_3$): δ 150.9, 125.4, 120.6 (d, J$_{C-N}$=3.2 Hz), 116.5 (d, J$_{C-N}$=17.6 Hz); $^{15}$N NMR (51 MHz, D$_2$O): δ 180.9; FTIR (thin film, DCM): 3142 (m, br), 2924 (m), 2213 (w), 1597 (s), 1410 (m), 1207 (s), 824 (s) cm$^{-1}$; HRMS-ESI (m/z): Calc'd for C$_6$H$_5$N$^{15}$N$^+$ ([M+H]$^+$): 106.0418; found: 106.0419.

2-(4-(bromomethyl)phenyl)-4,4,5,5-tetramethyl-1,3,2-dioxaborolane (2)

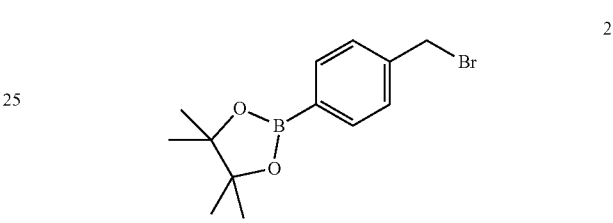

To a 50-mL round-bottomed flask was added PPh$_3$ (1.57 mg, 6.0 mmol, 2.0 equiv), CBr$_4$ (1.99 g, 6.0 mmol, 2.0 equiv) and THF (15 mL). The resulting mixture was cooled to 0° C. and (4-(4,4,5,5-tetramethyl-1,3,2-dioxaborolan-2-yl)phenyl)methanol (1) (702 mg, 3.0 mmol, 1.0 equiv) was added dropwise. The reaction was allowed to cool to room temperature, then stirred for 2 h, at which point TLC analysis indicated consumption of the alcohol. To the flask was added H$_2$O (30 mL) and extracted with EtOAc (30 mL×3). The combined organic layers were dried over Na$_2$SO$_4$, filtered, and the filtrate was concentrated. The crude mixture was subjected to silica gel chromatography (100% hexanes-5% EtOAc/hexanes) to afford 2 as an off-white solid (586 mg, 66%). $^1$H NMR (500 MHz, CDCl$_3$): δ 7.78 (d, J=8.0 Hz, 2H), 7.39 (d, J=8.0 Hz, 2H), 4.49 (s, 2H), 1.34 (s, 12H); matches reported spectra[1]

1-(4-boronobenzyl)-4-(cyano)pyridin-1-ium ($^{15}$N-BBCP)

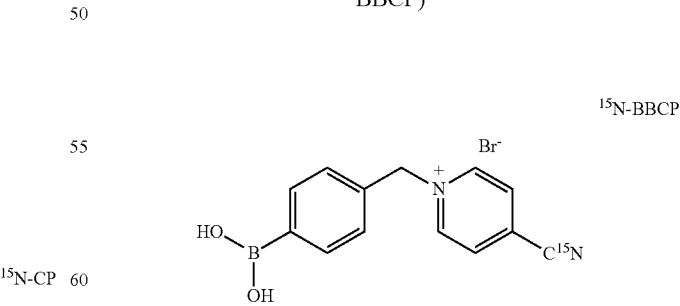

To a 25-mL round-bottomed flask was added $^{15}$N-4-cyanopyridine (70 mg, 0.67 mmol, 1.0 equiv), 2 (237 mg, 0.80 mmol, 1.2 equiv) and MeCN (3.5 mL). The resulting mixture was heated to 80° C. with a reflux condenser for 18 h. Then, to the mixture was added H$_2$O (10 mL) and further heated for 30 minutes. The reaction was allowed to cool to room temperature and the volatile solvent was removed in vacuo. The remaining solution washed with 1:1 hexanes/EtOAc (10 mL×3). The aqueous layer was frozen and lyophilized to afford $^{15}$N-BBCP as an off-white solid, as a hydrolyzed boronic acid form (182 mg, 85%). $^1$H NMR (500 MHz, D$_2$O): δ 9.22 (d, J=6.5 Hz, 2H), 8.51 (d, J=6.5 Hz, 2H), 7.86 (d, J=7.8 Hz, 2H), 7.54 (d, J=7.8 Hz, 2H), 5.97 (s, 2H); $^{13}$C NMR (126 MHz, D$_2$O): δ 145.9, 134.7, 133.8, 131.4, 128.8, 128.5, 114.2 (d, $J_{C-N}$=18.6 Hz), 65.6; $^{15}$N NMR (51 MHz, D$_2$O): δ 194.8; FTIR (neat): 3298 (m, br), 3025 (m), 2234 (w), 1635 (m), 1451 (s), 809 (s) cm$^{-1}$; HRMS-ESI (m/z): Calc'd for $C_{13}H_{12}{}^{11}BN^{15}NO_2{}^+$ (M$^+$): 240.0957; found: 240.0963.

Example 2: Biochemical Analysis of BBCP

Figure 1B:
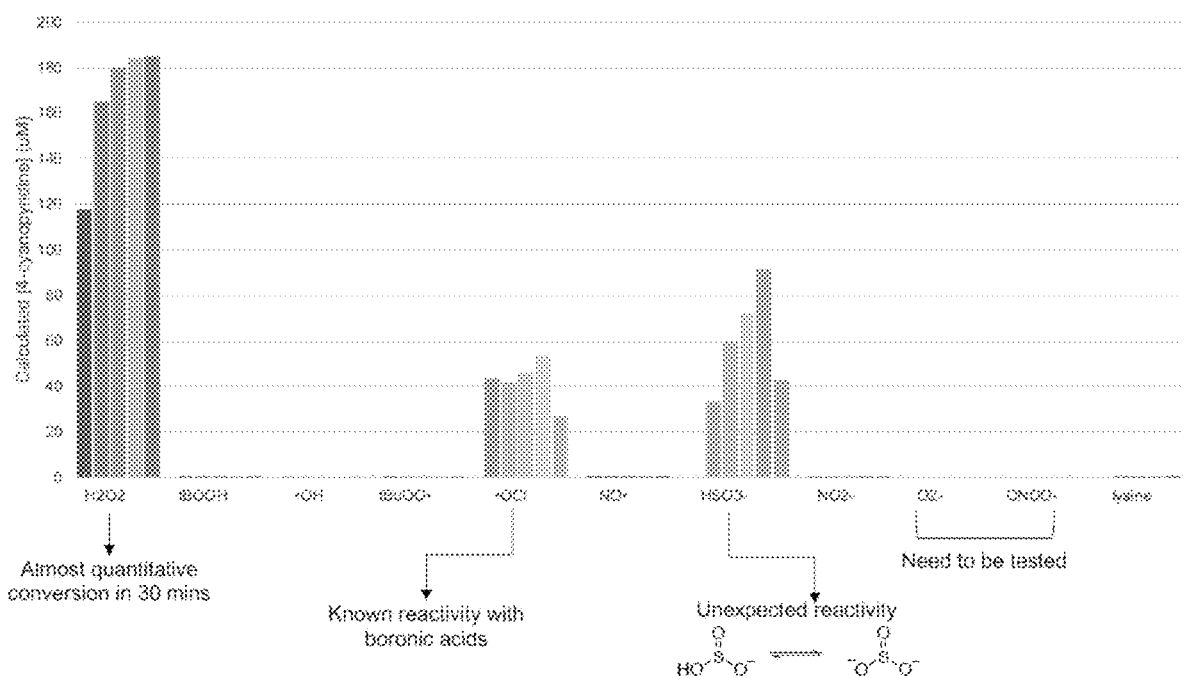
FIG. 1B shows results of $^{15}N$-BBCP selectivity test with reactive oxygen/nitrogen/sulfur species. ROS/RNS selectively tests were performed under the following conditions: 200 μM probe, 2 mM (10 equivalents) of reactive species in PBS buffer at pH 7.4. Concentrations of 4-cyanopyridine were measured by LCMS after 5, 10, 15, 30, and 60 minutes using a calibration curve.
Figure 4:
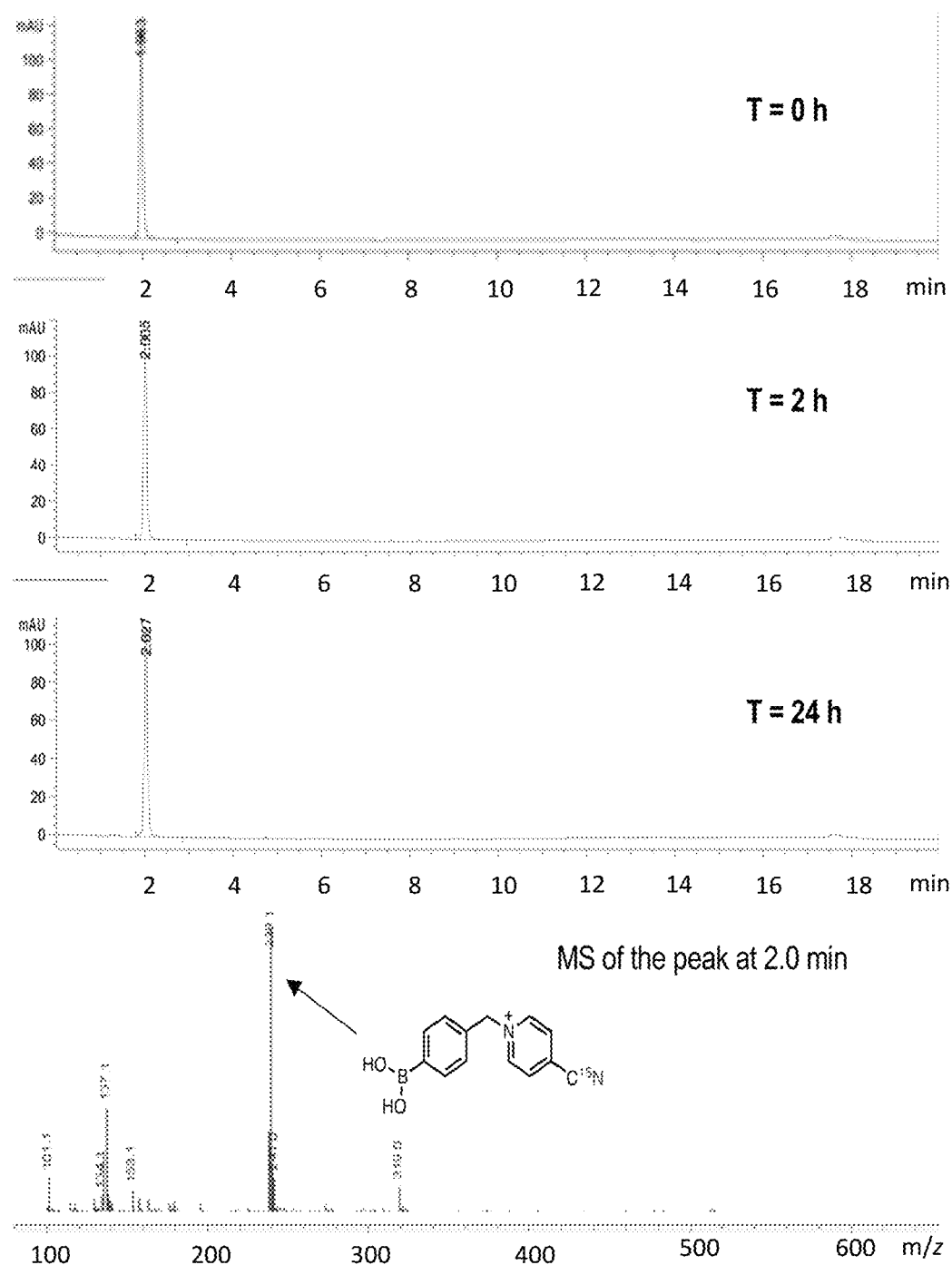
FIG. 4 shows liquid chromatogram of BBCP (200 μM) after 0, 2 and 24 h of incubation in phosphate buffer saline (PBS, pH 7.4) and mass spectra of the peak at 2.0 min.

The applicability of $^{15}$N-BBCP for hyperpolarized imaging in animal models was investigated. BBCP demonstrated high aqueous solubility and stability in physiological buffer solution (PBS, pH 7.4), only showing hydrolysis of boronic ester to boronic acid (FIG. 4). The selectivity toward H$_2$O$_2$ over other biologically relevant reactive oxygen and nitrogen species (ROS/RNS) was examined. Upon reaction of BBCP with ROS/RNS for various timepoints (5-30 min) at room temperature, only the reaction with H$_2$O$_2$ showed a significant conversion to 4-cyanopyridine based on LC/MS analysis (FIG. 1A) Unexpectedly, BBCP also showed reactivity toward hydrogensulfite (HSO$_3{}^-$, FIG. 1B). In addition, hypochlorite (OCl$^-$) and peroxynitrite (ONOO$^-$) showed moderate reactivity with BBCP, in which reactions of aryl boronates with OCl$^-$ and ONOO$^-$ have been reported. However, the physiological concentration of peroxynitrite is much lower (~1 nM for [ONOO$^-$] vs 100 nM for [H$_2$O$_2$]), which will allow the use of BBCP as a selective H$_2$O$_2$ sensing probe.

Figure 2:
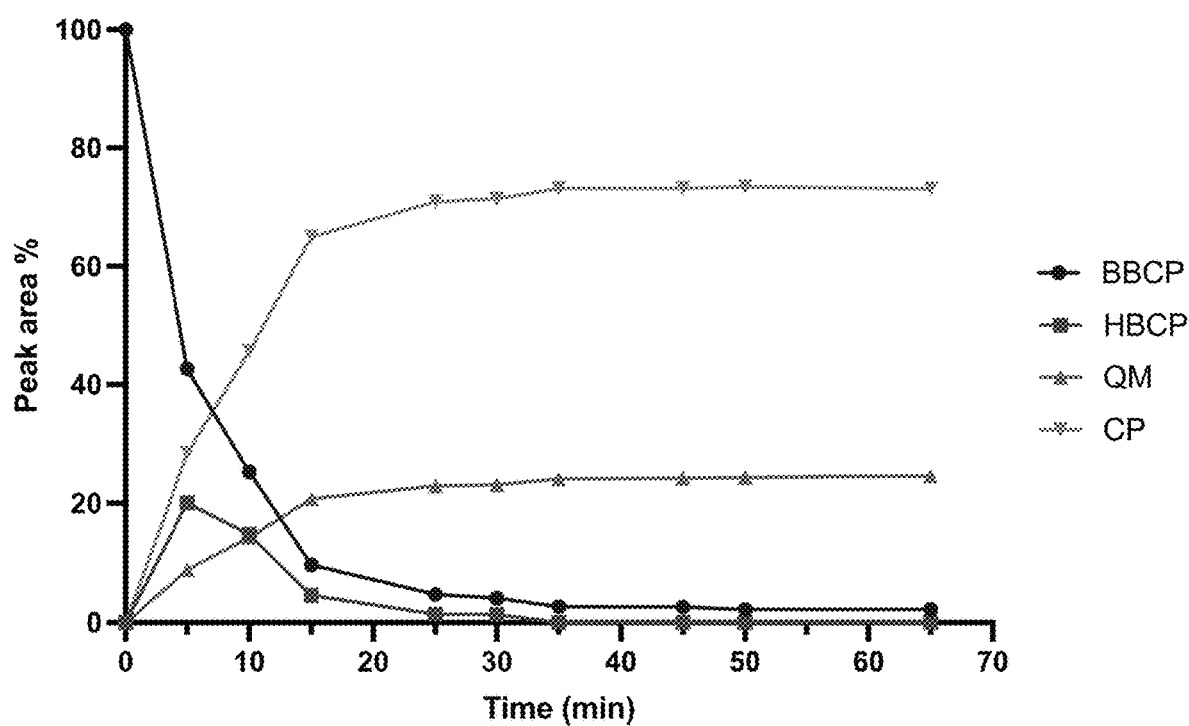
FIG. 2 shows LC/MS trace data of reactions of BBCP (200 μM)+$H_2O_2$ (1 mM, 5 equiv.) in PBS (pH 7.4) after 5-65 min. Peak area in reference to BBCP at Abs=280 nm.
Figure 3:
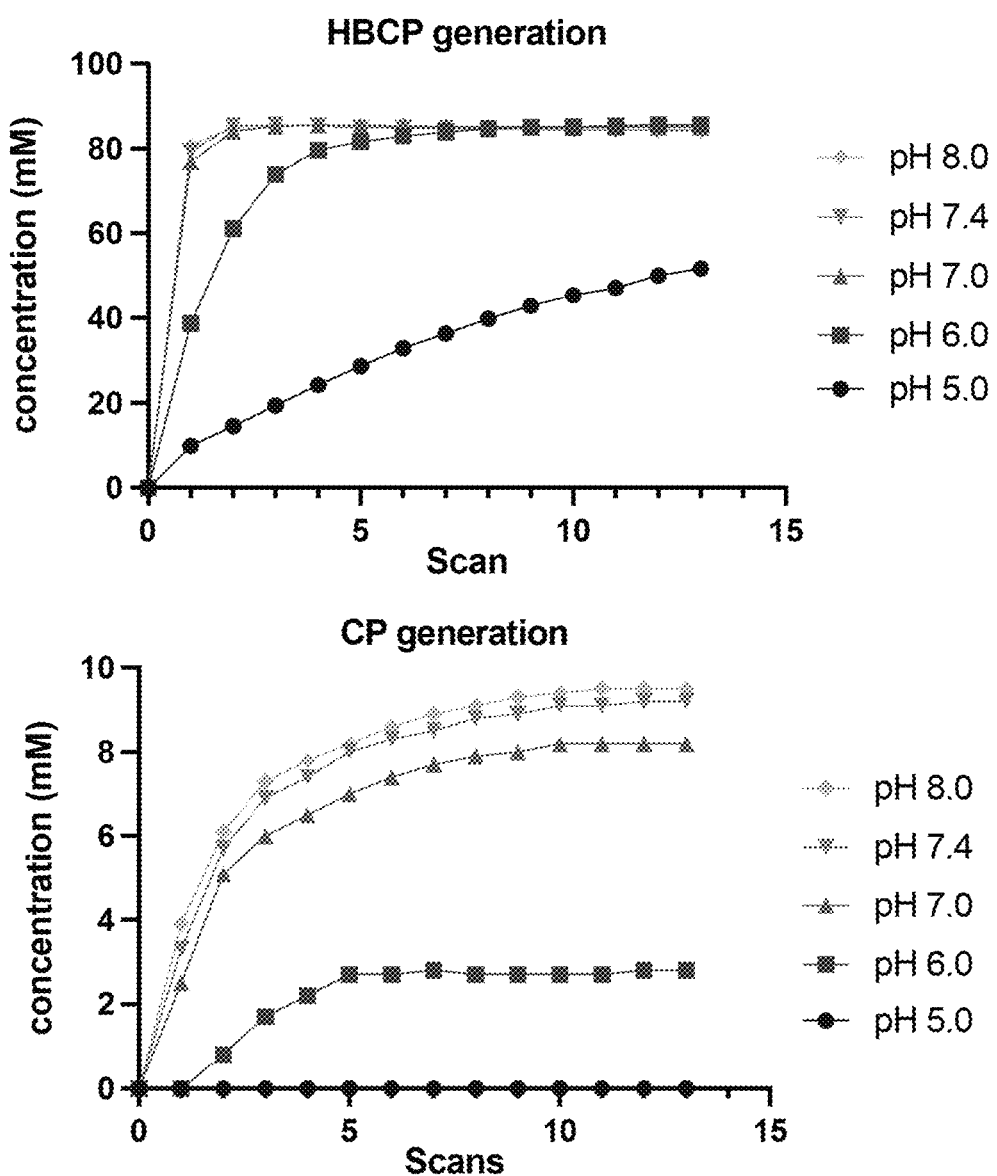
FIG. 3 shows effects of buffer pH on oxidation and fragmentation rates. BBCP (100 mM) reaction with 1 equiv. $H_2O_2$ in PBS+10% $D_2O$ was monitored by $^1H$ NMR.
Figure 5A:
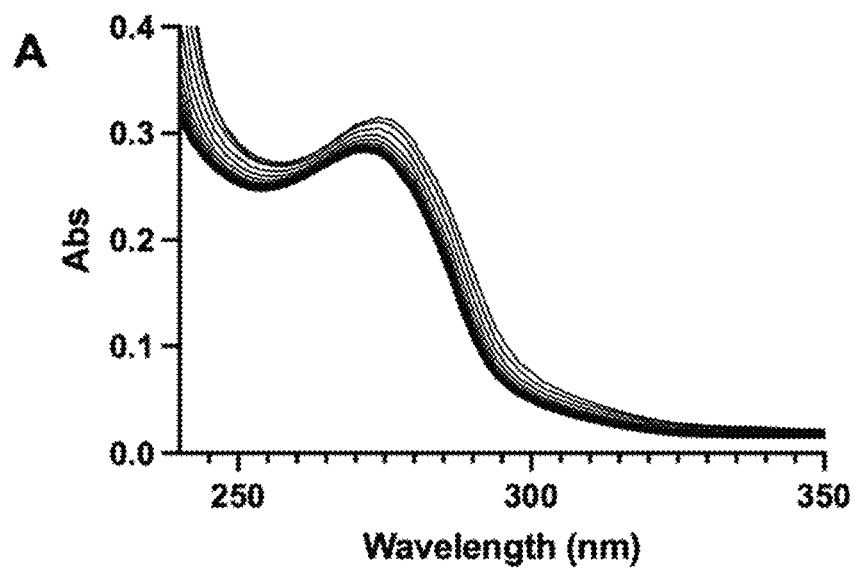
FIGS. 5A-5B shows representative results of kinetics measurement of the rate of reaction between BBCP and $H_2O_2$.
Figure 5B:
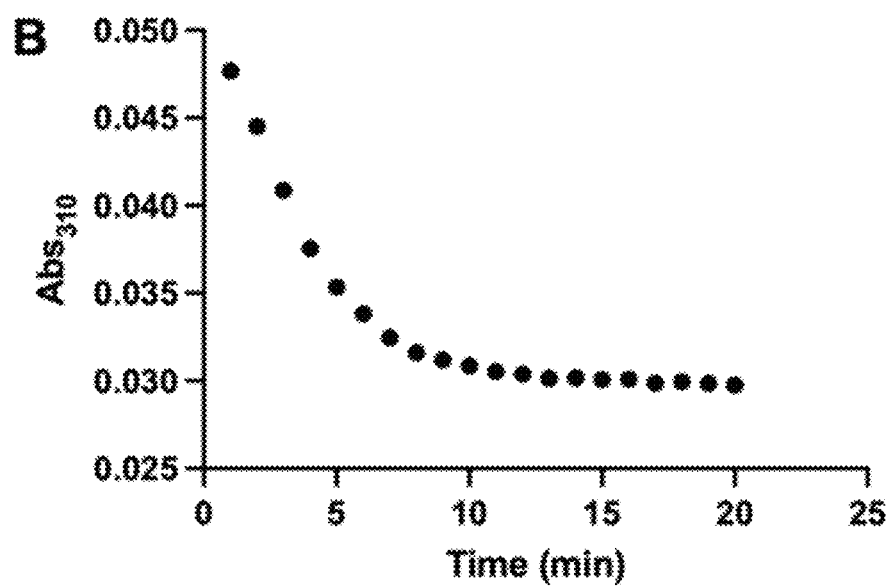

The reaction mechanism of BBCP with H$_2$O$_2$ was investigated. Treatment of BBCP with H$_2$O$_2$ generated 4-cyanopyridine (CP) and quinone methide (QM), with transient phenol species (HBCP) according to the LC/MS study (FIG. 2), suggesting the proposed two-step oxidation and fragmentation as the sensing mechanism. The UV/Vis kinetic measurements revealed that the reaction of BBCP with H$_2$O$_2$ proceeds rapidly with a second-order rate constant of $k_2$=12.6±0.52 M$^{-1}$ min$^{-1}$ (25° C., PBS pH 7.4) (FIGS. 5A and 5B). Interestingly, the oxidation and fragmentation rates were dependent on the pH of the reaction solution. Investigation of the effects of buffer pH revealed the oxidation rate is slowed at pH <6.0, and the fragmentation rate was impeded to a greater extent in acidic solutions. These data suggest $^{15}$N-BBCP may be used for the analysis of pH-dependent H$_2$O$_2$ sensing (FIG. 3).

Figure 6A:
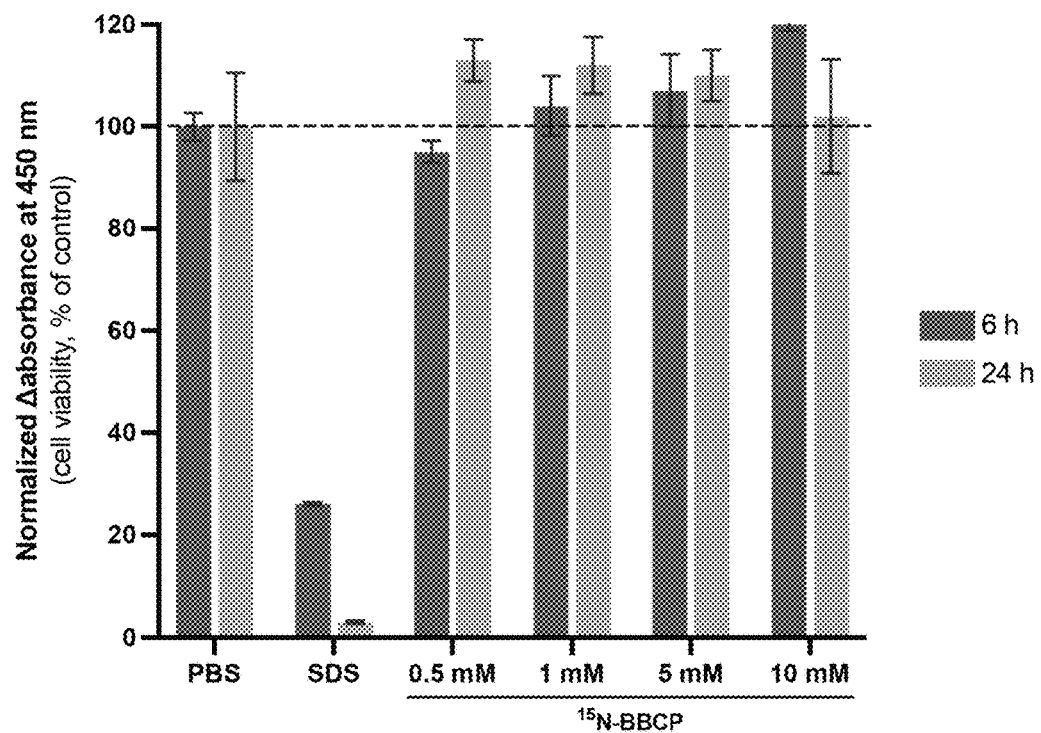
FIG. 6A shows results of cytotoxicity analysis of BBCP using WST-8 assay. HeLa cells treated with 0.5, 1, 5 and 10 mM of BBCP and incubated for 6 and 24 h. The absorbance normalized to show cell viability. The error bars indicate s.d. (N=3).
Figure 6B:
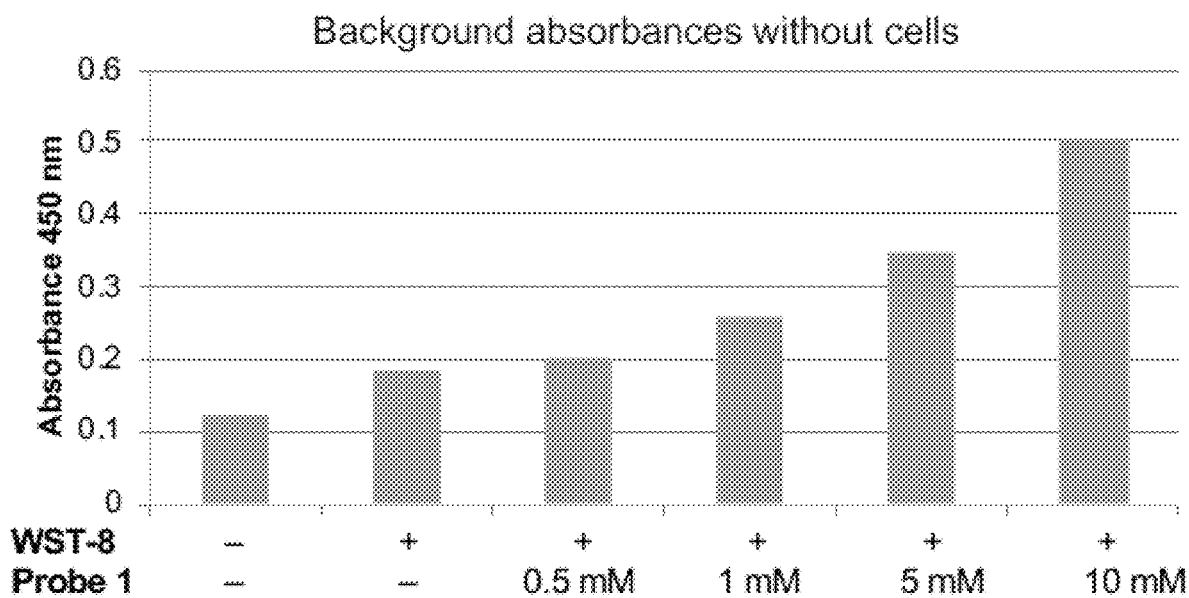
FIG. 6B shows results for $^{15}N$-BBCP cytotoxicity test with HeLa cells using a WST-8 assay. Stock solutions of the probe (5, 10, 50, and 100 mM) in PBS were prepared and 10 μL of stock solutions were added to wells of a 96 well plate so that the final treated concentrations are 0.5, 1, 5, and 10 mM in triplicates. Phosphate buffer solution (10 μL) was used as a negative control and sodium dodecyl sulfate (1 mM, 10 μL) was used as a positive control. Background absorbances without cells but with cellular growth media, DMEM, were measured to subtract background absorbance.

The cytotoxicity of BBCP was evaluated as HP molecular probes are commonly injected into animal models in high concentrations (20-100 mM) to account for ~10-fold dilution in blood. Cytotoxicity assay showed BBCP has minimal toxicity (>90% cell viability) at concentrations up to 10 mM after 6 h of treatment (FIGS. 6A and 6B). Altogether, these results illustrate BBCP has favorable properties as a molecular imaging agent, including high aqueous solubility/stability, high ROS selectivity, fast reaction kinetics, and low cytotoxicity. These desirable factors of $^{15}$N-BBCP allowed translation to in vivo HP imaging.

ROS Selectivity Tests.

Selectivity for the BBCP probe was measured by analytical high performance liquid chromatography (HPLC) using Agilent 1200 Series HPLC System equipped with a multi-wavelength detector and an Agilent Zorbax SB-C18 Column (3.5 μm particle size, 3.0×150 mm). Concentrations of 4-cyanopyridine was calculated using integrated peak intensities at 280 nm using a calibration curve. All reactions were tested with 200 μM BBCP and 2 mM ROS/RNS (10 equiv) in PBS (pH 7.4). At a given time point, the reaction was quenched with 10 μL 1 M ascorbic acid (10 mM) and analyzed by LCMS. The ROS and RNS were generated as follows:

H$_2$O$_2$: A 30% H$_2$O$_2$ in H2O solution was diluted to a 500 mM stock solution. 4 μL of 500 mM H$_2$O$_2$ (2 mM) was added to a 200 μM of BBCP in PBS.

tBuOOH: A 70% tBuOOH in H$_2$O solution was diluted to 500 mM. Followed same procedure as H$_2$O$_2$, with final concentration of 2 mM of tBuOOH.

OH.: PBS and MeOH degassed for ~15 mins before using. 20 μL of 0.5 M iron (II) sulfate in PBS was added, followed by 4 μL of 500 mM H$_2$O$_2$.

tBuO.: PBS and MeOH degassed for ~15 mins before using. 20 μL of 0.5 M iron (II) sulfate in PBS was added, followed by 4 μL of 500 mM tBuOOH.

OCl$^-$: Commercial bleach (8.25% NaOCl) was diluted to 500 mM. 4 μL of 500 mM NaOCl (for a final concentration of 2 mM) was added to 200 μM of BBCP.

NO: NO was generated from NOC-5 (1.0 equiv NOC-5 generates 2.0 equiv of nitric oxide, $t_{1/2}$ in pH 7.4=93 min). 40 μL of 50 mM stock of NOC-5 in PBS was added to individual vial (2 mM). Allowed to sit for 93 min (aiming for 2 of NOC-5 to decompose into 2 mM NO) before addition of 4 μL of 50 mM BBCP.

NO$_2{}^-$: Commercial sodium nitrite was used to make a 500 mM stock solution in H$_2$O. 4 μL of 500 mM NaNO$_2$ (for a final concentration of 2 mM) was added to a 200 μM of BBCP.

O$_2{}^-$: Superoxide was prepared using KO$_2$ stock made in DMSO.

ONOO$^-$: To a solution of aqueous NaOH (0.5 M, 2.5 mL) and iPrOH (2.5 mL) was added H$_2$O$_2$ (30% in H$_2$O, 0.12 mL, 1.2 mmol, 1.2 equiv), followed by isoamyl nitrite (0.135 mL, 1.0 mmol, 1.0 mmol). The reaction was stirred at room temperature for 20 mins and washed with CH$_2$Cl$_2$ (10 mL×2). MnO$_2$ was added to the aqueous layer to scavenge unreacted H$_2$O$_2$, which resulted in bubbling. The solution was then filtered and stored in −20° C. until use. The concentration of the stock solution was calculated to be 14.3 mM using absorbance at 302 nm (e=1670 M$^{-1}$).

Aqueous Solubility and Stability of $^{15}$N-BBCP

Solubility of $^{15}$N-BBCP in DI H2O was 0.2-0.25 M at room temperature. Solubility of $^{15}$N-BBCP in PBS (pH 7.4) was about 200 mM (maximum concentration tested) at 37° C. Boronic ester hydrolyzes to boronic acid in PBS (at least in LCMS conditions) (Scheme 3). The probe (200 μM) was stable in PBS and DMEM media (pH 7.4) at room temp for over 26 h, as shown by LCMS absorbance of the probe in PBS over time (peak area at 0, 2, and 26 hours are 566.6, 565.6, and 564.9, respectively).

Scheme 3: Hydrolysis of $^{15}$N-BBCP in PBS buffer.

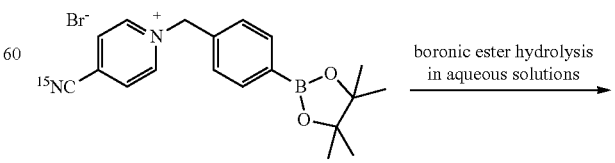

MW (with Br): 402.1 g/mol
MW (withoud Br): 322.20 g/mol

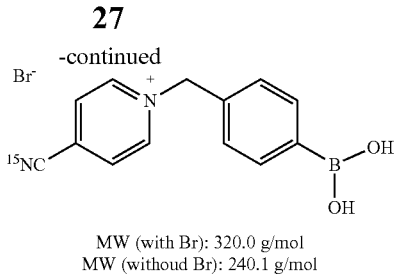

MW (with Br): 320.0 g/mol
MW (withoud Br): 240.1 g/mol

LC/MS Study of BBCP Oxidation Mechanism

BBCP (200 µM) was reacted with $H_2O_2$ (1 mM, 5 equiv) in PBS (pH 7.4) and monitored by LCMS after 5-60 min of reaction. The phenol intermediate, quinone methide and 4-cyanopyridine peaks were identified by their corresponding mass spectra. The peak area (%) change was monitored using BBCP as the reference (100%), therefore only qualitative not quantitative.

UV/Vis Kinetics Measurement

The pseudo-first order rate constant was calculated by monitoring the BBCP consumption with UV/Vis spectroscopy over time in the presence of excess $H_2O_2$. A solution of BBCP (50 µM) oxidation was initiated by the addition of freshly prepared $H_2O_2$ (5 mM, 100 equiv) in PBS (pH 7.4) at 25° C. Reactions were monitored as $Abs_{310}$ change and scanned every 30 s for 20 minutes. The apparent $k_1$ value was determined by the initial rate of reaction (0-50 s) as $(3.4\pm0.15)\times10^{-3}$ $min^{-1}$. The experiment was repeated in triplicate to give a $k_2$ value of $12.6\pm0.52$ $M^{-1}$ $min^{-1}$ $(0.21\pm0.0087$ $M^{-1}$ $s^{-1})$.

Investigation of Buffer pH on Reaction Rates

To a solution of BBCP (100 mM, 500 µL) in PBS (various pH)+10% $D_2O$ in an NMR tube was added $H_2O_2$ (2.5 M, 20 ILL). The reaction was immediately scanned continuously by $^1H$ NMR over time, to generate a total of 13 spectra and reaction time of ~30 minutes for each experiment. The concentration of the oxidation product, HBCP, and fragmentation product, CP, were calculated using the $^1H$ NMR spectra.

Cytotoxicity Analysis Using WST Assay.

WST cytotoxicity assay was performed using Cell Counting Kit-8 (CCK-8) according to the procedure as follows. HeLa cells were seeded in a 96-well plate at a concentration of 5000 cells/well in DMEM medium (high glucose) supplemented with 10% FBS and 1% sodium pyruvate. The cell cultures were incubated for 24 h in a humidified atmosphere of 5% $CO_2$ at 37° C. After the incubation period, 10 µL of 5, 10, 50, 100 mM stock solutions of BBCP dissolved in PBS buffer (pH 7.4) were added to each well so the final concentration is 0.5, 1, 5, 10 mM, respectively. PBS and sodium dodecyl sulfate (SDS) (1 mM) were used as negative and positive controls, respectively. The treated 96-well plates were incubated for 6 and 24 h in a humidified atmosphere of 5% $CO_2$ at 37° C. After appropriate incubation time, the CCK-8 solution (10 µL) was added to each well and further incubated for 2 h for color development. The absorbance at 450 nm from each well was measured by using a microplate reader (Synergy™ H1, BioTek). The background absorbance of BBCP corrected.

Example 3: In Vitro and In Vivo Applications of $^{15}N$-BBCP

Dynamic Nuclear Polarization of 15N-BBCP

Hyperpolarization lifetime and efficiency of $^{15}N$-BBCP were investigated. A solution of $^{15}N$-BBCP (3.4 M, 4:1 DMSO:glycerol with 15 mM Ox063) was polarized using a SPINlab (GE Healthcare) polarizer, which relies on nuclear spin polarization transfer from electrons to the $^{15}N$ nuclei via microwave irradiation at low temperatures (1-2 K). The frozen polarized sample was rapidly dissolved in 6 mL dissolution buffer (0.1 g/L EDTA, pH=7.4 in DI water) to afford a biocompatible hyperpolarized solution.

Spin-lattice relaxation time ($T_1$) of IP $^{15}N$-BBCP solution was measured at 1T and 3T using a benchtop $^{15}N$ NMR spectrometer (Spinsolve; Magritek) and a clinical MRI scanner (Achieva; Philips Healthcare), respectively. A dynamic non-selective pulse-and-acquire sequence with 10° flip angle was used (TR=10s for 1T, 5s for 3T). The $T_1$ was calculated by fitting the decay curve to a mono exponential function after correcting the RF sampling loss. At 3T, a $^{15}N/^1H$ dual-tuned half-pipe rat birdcage coil (Clinical MR solutions) was used. In vivo studies were performed using a Wistar rat (350 g) at the 3T scanner using the same protocol.

Figure 7:
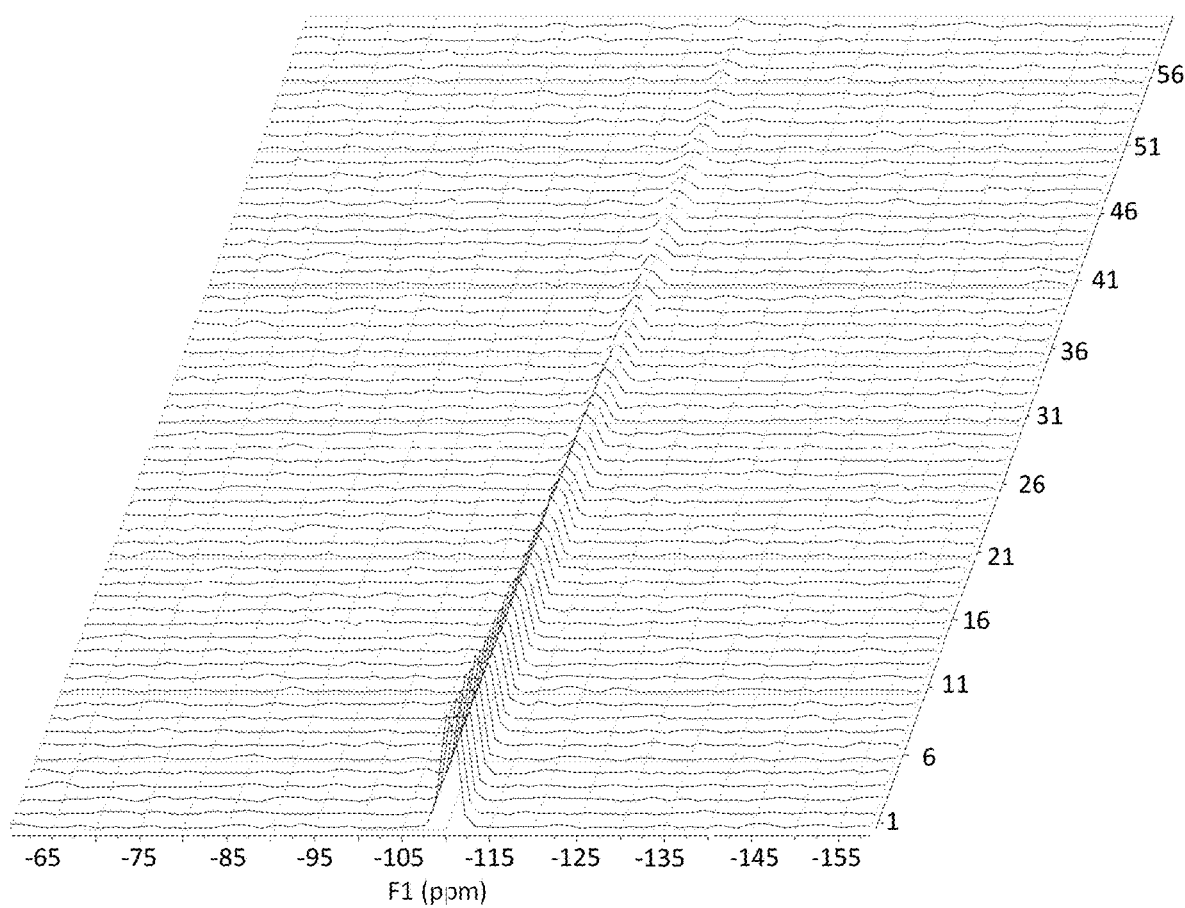
FIG. 7 shows representative in vitro time series of HP $^{15}N$-BBCP spectra, as a result of hyperpolarization of $^{15}N$-BBCP.
Figure 8A:
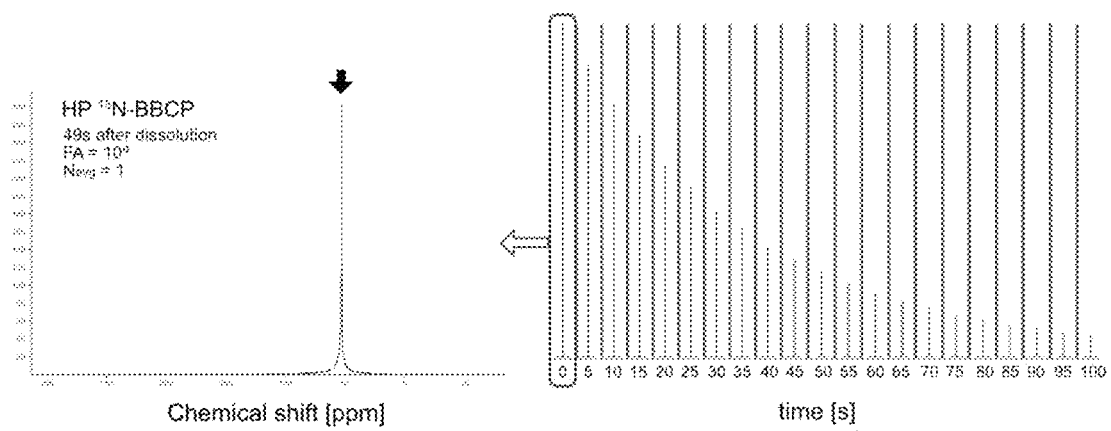
FIG. 8A shows representative time series of HP $^{15}N$-BBCP at 3T and the first timepoint $^{15}N$ spectrum in an in vitro $T_1$ and polarization level measurement.
Figure 8B:
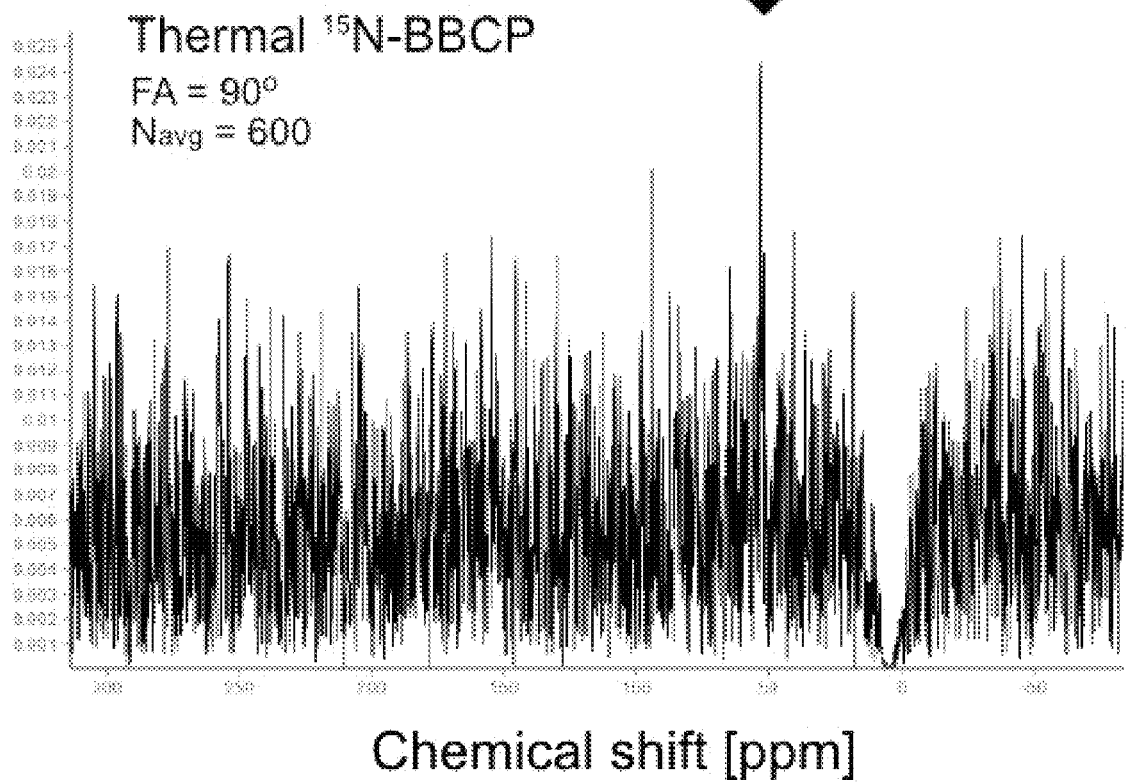
FIG. 8B shows representative thermal scan of the $^{15}N$-BBCP solution in an in vitro $T_1$ and polarization level measurement.
Figure 8C:
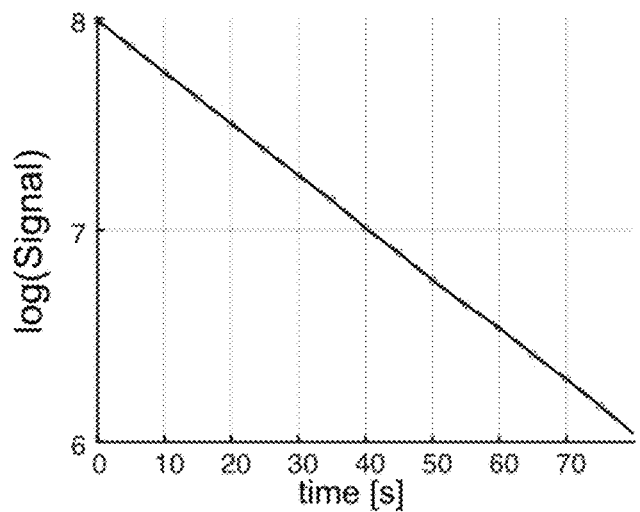
FIG. 8C shows estimation (−1/slope) of the $T_1$ relaxation time in an in vitro $T_1$ and polarization level measurement.

The in vitro $T_1$ of $^{15}N$-BBCP was measured to be 340.1 s at 1 T and 41.2 s at 3 T, with a polarization level of 17.3% compared to thermal scans. Since the hyperpolarization experiments can record signals for up to ~3 times the $T_1$, such a long $T_1$ value allowed the $^{15}N$ signal to be detectable for an extended period in vitro (FIG. 7). FIG. 8A shows the $T_1$ decay of 20-mM HP $^{13}N$-BBCP at 3T. Thermally polarized signal was acquired by averaging 600 scans with 90° excitation (FIG. 8B). The SNR of HP $^{15}N$-BBCP at the first timepoint was 1333 and the polarization level calculated from the HP and thermal scans was estimated as 17.3% at dissolution.

Figure 9:
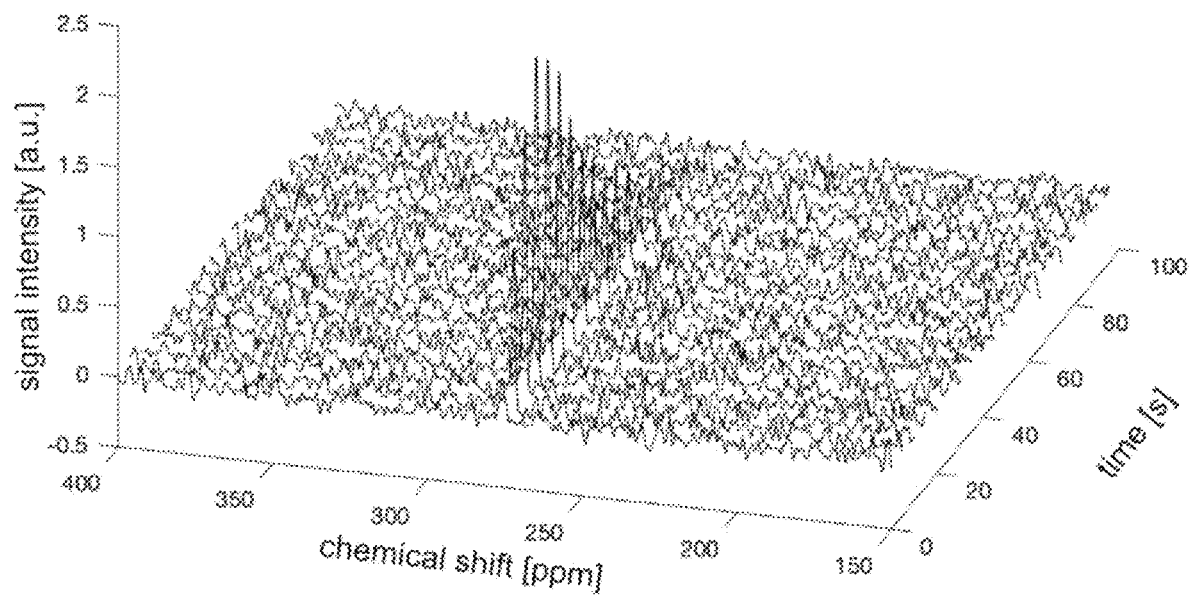
FIG. 9 shows representative results of in vivo observation of HP $^{15}N$-BBCP spectra acquired from a rat liver at 3 T, as a result of hyperpolarization of $^{15}N$-BBCP.
Figure 10:
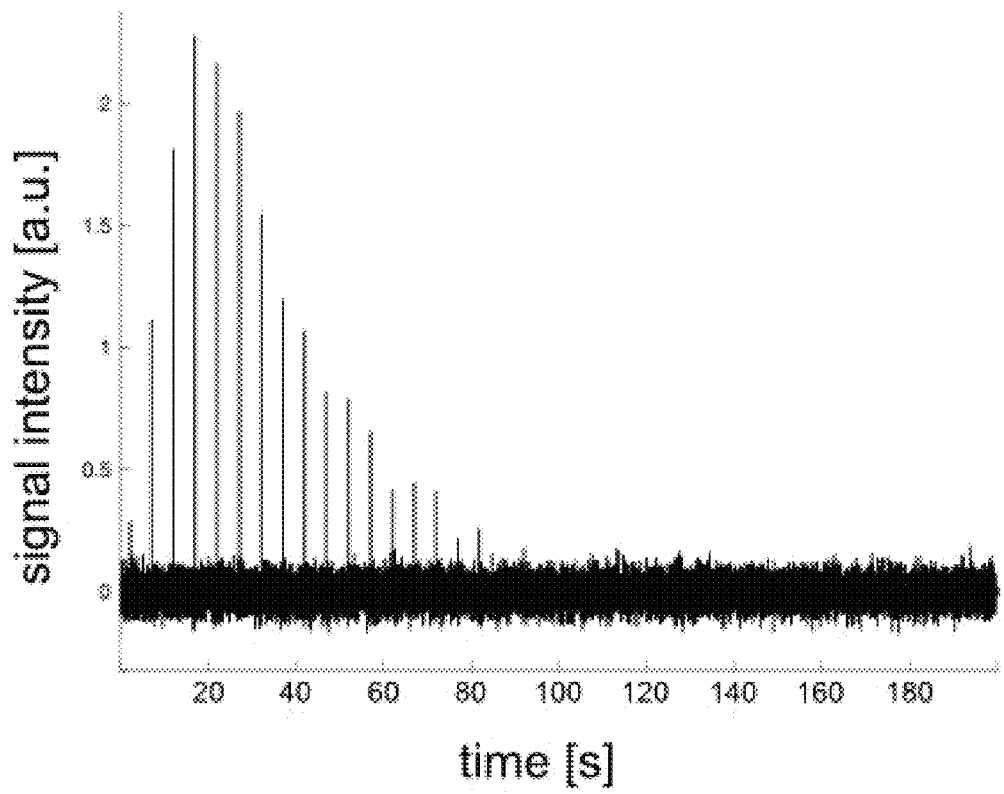
FIG. 10 shows temporal changes of HP $^{15}N$-BBCP peak at 276 ppm in an in vivo observation of HP $^{15}N$-BBCP in rat liver.

Additionally, HP $^{15}N$-BBCP signal was also obtained in vivo. The rat received a bolus injection of 20 mM HP $^{15}N$-BBCP (4.5 mL) at baseline and the $^{15}N$-BBCP peak was detected at 276 ppm in rat liver (FIG. 9 and FIG. 10). No metabolic products were observed above the noise level, presumably due to low $H_2O_2$ concentrations regulated by the native antioxidative responses in well-balanced physiological conditions.

Reaction-Based $H_2O_2$ Sensing Using Hyperpolarized $^{15}N$-BBCP

Figure 11:
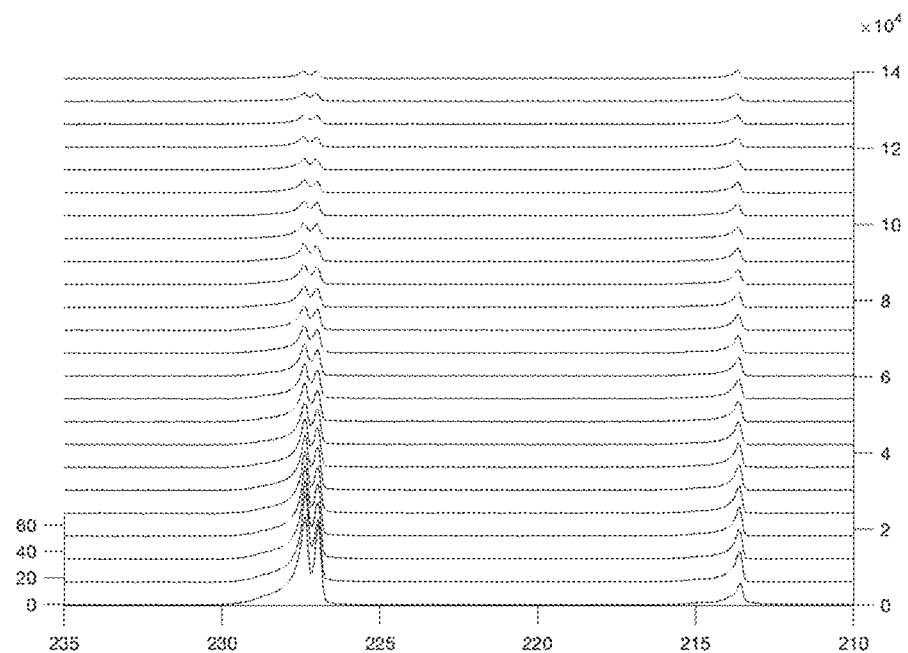
FIG. 11 shows representative results of chemical shift imaging for in vitro reaction-based detection of $H_2O_2$ as a result of hyperpolarization of $^{15}N$-BBCP, which demonstrates a two-step sensing mechanism.
Figure 12:
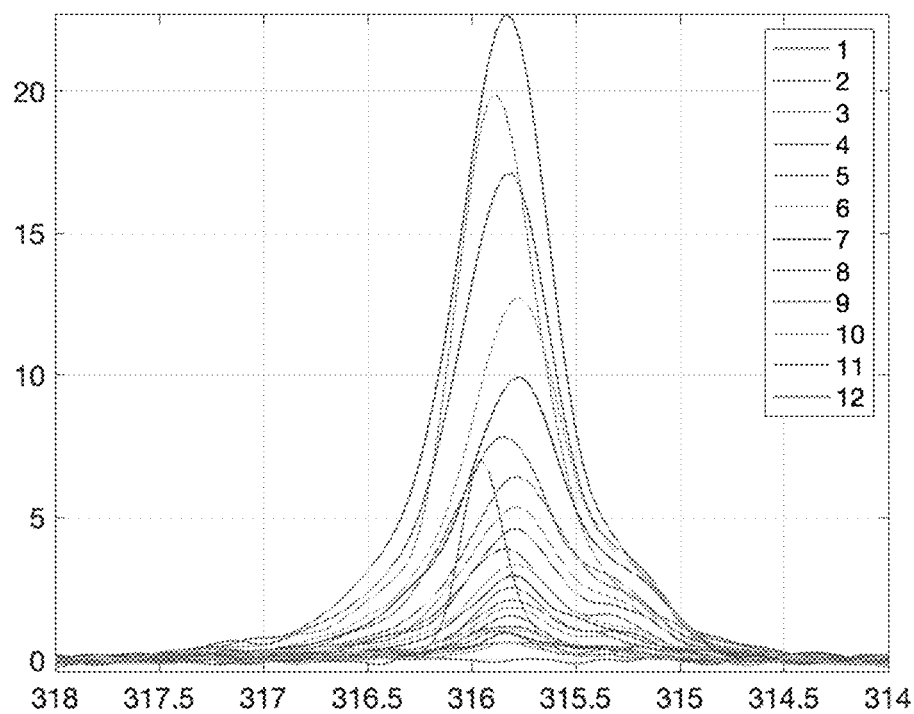
FIG. 12 shows representative results for in vivo reaction-based detection of $H_2O_2$ as a result of hyperpolarization of $^{15}N$-BBCP.

Hyperpolarized $^{15}N$-BBCP reaction with $H_2O_2$ in vitro was carried out to validate reaction-based chemical-shift imaging (FIG. 11). Immediately upon the addition of $H_2O_2$, hyperpolarized signals from $^{15}N$-BBCP and its oxidation product $^{15}N$-HBCP at 0.6 ppm upfield, as well as the fragmentation product $^{15}N$-CP signal identified at 13.8 ppm upfield, were observed. The in vitro scans show the two generated $^{15}N$-species can be used for HP chemical-shift imaging, yet $^{15}N$-CP would offer a greater signal sensitivity. Nonetheless, this study suggests that both oxidation and fragmentation occur rapidly and the $T_1$ values of each $^{15}N$-species are sufficiently long enough to monitor the $H_2O_2$ sensing reactions in real-time.

Finally, the ability of $^{15}N$-BBCP to image $H_2O_2$ in vivo using clinical 3 T MRI was assessed. Considering the HP $^{15}N$-BBCP presented in a healthy rat liver did not provide detectable metabolic products (FIG. 9), $^{15}N$-BBCP reaction in vivo with an injection of exogenous $H_2O_2$ into the rat to imitate an oxidative burst was assessed. Remarkably, $^{15}N$-MRS scans in a rat showed $^{15}N$-BBCP signal, and $^{15}N$-HBCP peak was detectable despite the small chemical shift difference. However, $^{15}N$-CP was not observed, in which the low reaction conversion may be attributed to rapid antioxidant responses in vivo that lowers accessible $H_2O_2$. $^{15}N$-BBCP is the first designed reaction-based $^{15}N$-probe demonstrated in vivo.

Example 4: In Vitro and In Vivo Applications of $^{15}$N-BBCP

Dynamic Nuclear Polarization of $^{15}$N-BBCP

Figures 13A, 13B:
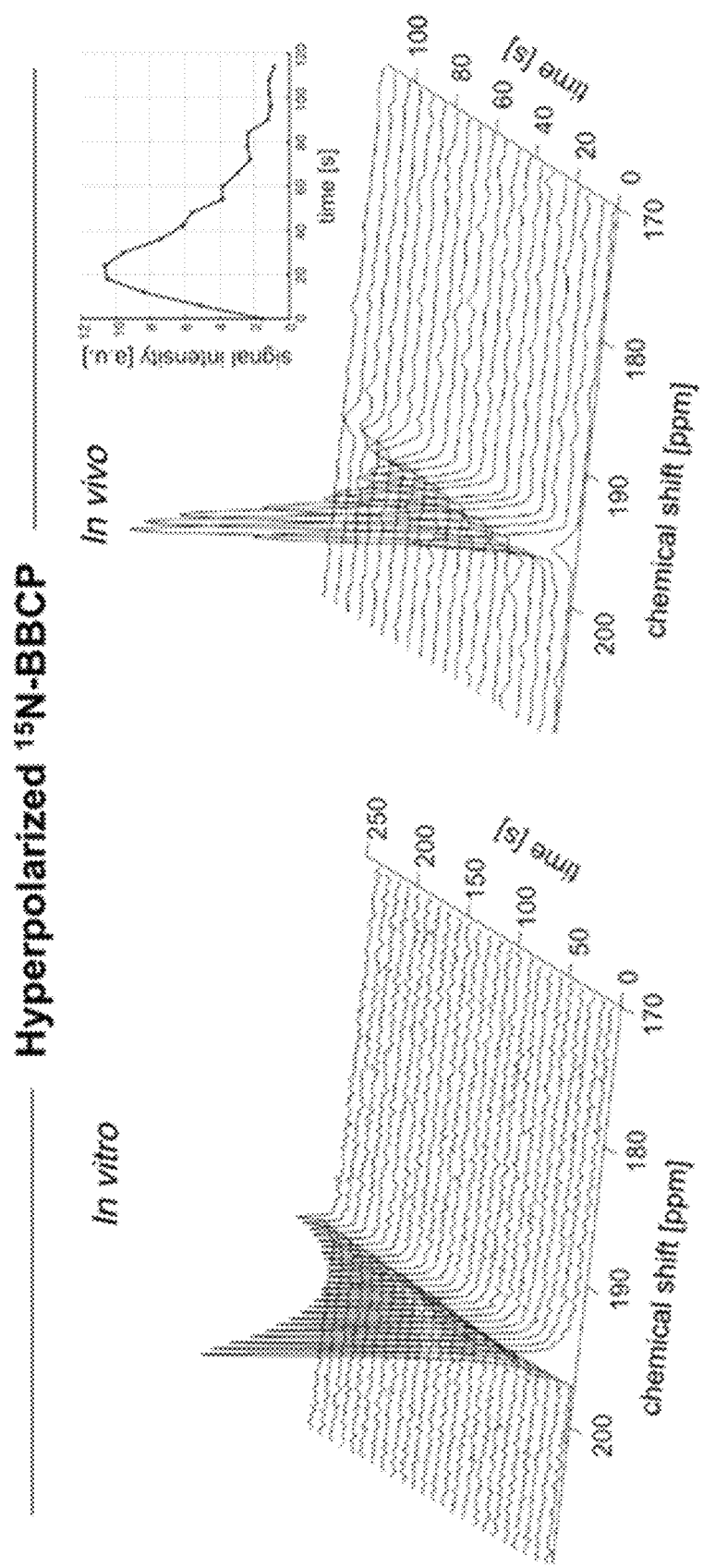
FIGS. 13A-13E shows representative results showing hyperpolarization of $^{15}N$-BBCP and a two-step sensing mechanism of $H_2O_2$.

Polarization level and $T_1$ relaxation time of $^{15}$N-BBCP were estimated in vitro. $^{15}$N-BBCP samples (3.4 M, 4:1 DMSO:glycerol with 15-mM Ox063) were prepared and polarized using a SPINlab™ DNP polarizer (GE Healthcare) that operates at ~0.8 K and 5 T. After 3-4 h of polarization, the frozen sample was rapidly dissolved in hot (130° C.) dissolution media (0.1 g/L EDTA, pH=7.4 in DI water), producing 5.5-6.0 mL of 20-mM hyperpolarized $^{15}$N-BBCP solution. The in vitro $T_1$ of $^{15}$N-BBCP was estimated as 340.1 s at 1 T (Spinsolve, Magritek) and 122.8 s at 3 T (Achieva, Philips Healthcare) after correcting radiofrequency (RF) sampling losses (FIG. 13A). The liquid-state polarization level at the time of dissolution was estimated as 17.3% from the 3 T data by comparing to thermal scans. Hyperpolarized signal was retained when 40-mM hyperpolarized $^{15}$N-BBCP was injected to healthy rats as a bolus (FIG. 13B). No metabolic products were observed presumably due to low $H_2O_2$ concentrations regulated by the native antioxidative responses in well-balanced physiological conditions.

Reaction-Based $H_2O_2$-Sensing Using Hyperpolarized $^{15}$N-BBCP

Figure 13C:
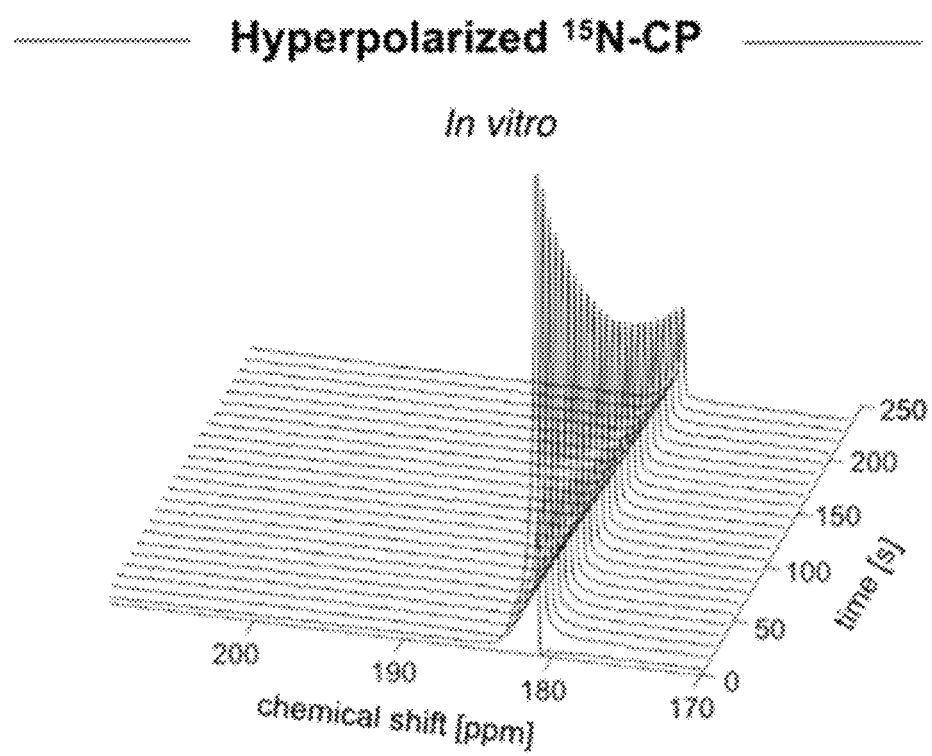
Figures 13D, 13E:
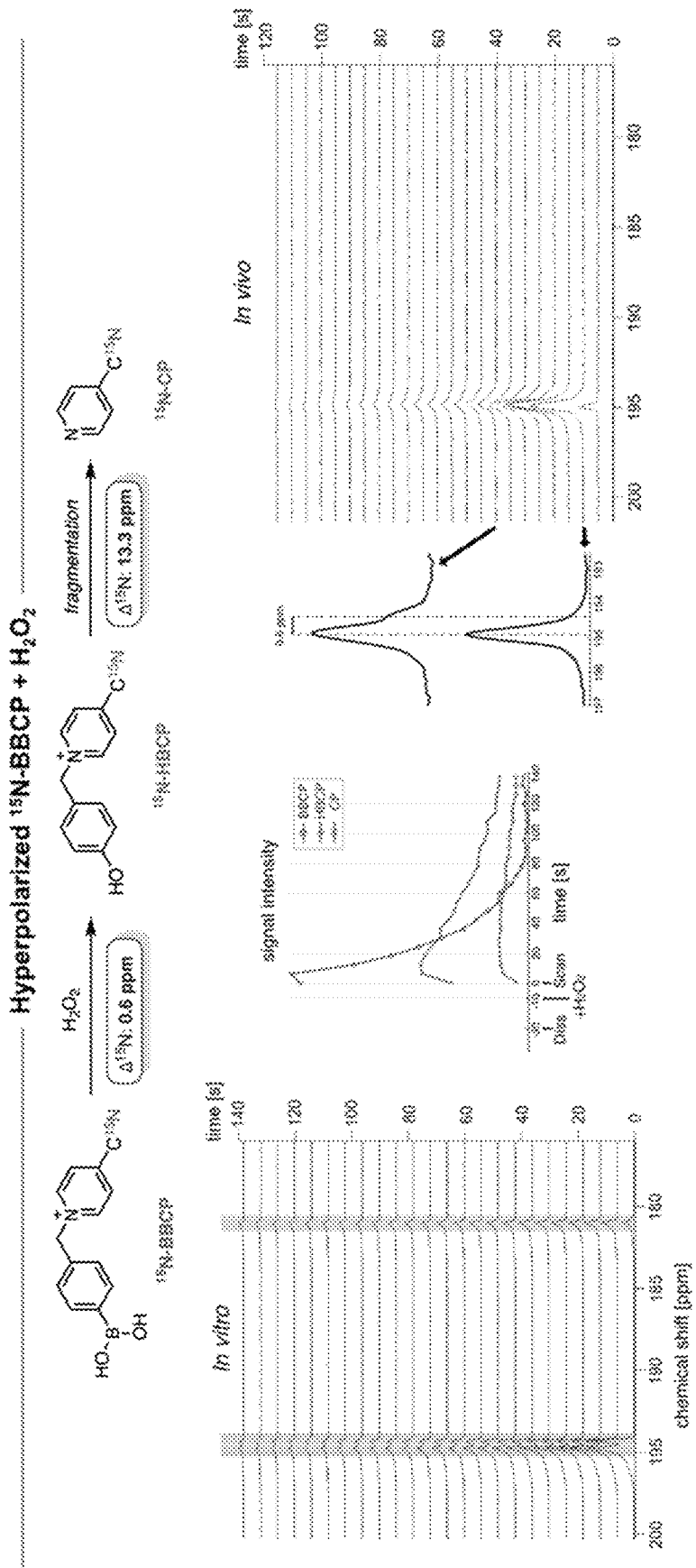

Hyperpolarized $^{15}$N-BBCP was further tested with $H_2O_2$ in vitro to validate its reaction-based $H_2O_2$-sensing performance (FIG. 13D). Immediately upon the addition of $H_2O_2$, hyperpolarized signals from $^{15}$N-BBCP as well as its oxidation product, $^{15}$N-HBCP at 0.6 ppm upfield, and the fragmentation product, $^{15}$N-CP at 13.9 ppm upfield, appeared, demonstrating that both oxidation and fragmentation occur rapidly and the $T_1$ values of $^{15}$N-species are sufficiently long to monitor the $H_2O_2$-sensing reactions in real-time. A separate in vitro experiment with hyperpolarized $^{15}$N-CP confirmed the long $T_1$ of $^{15}$N-CP (184.3 s) at 3 T (FIG. 13C).

Finally, the feasibility of $^{15}$N-BBCP to detect $H_2O_2$ in vivo was investigated in a rat model at the clinical 3 T MRI. With an intravenous bolus injection of 40-mM hyperpolarized $^{15}$N-BBCP, following an intraperitoneal injection of $H_2O_2$, both $^{15}$N-BBCP and $^{15}$N-HBCP peaks appeared from the imaging slab that included the liver and kidneys (FIG. 13E). Despite the small chemical shift difference, the accumulation of $^{15}$N-HBCP production was clearly observed in the later time points. Considering the hyperpolarized $^{15}$N-BBCP presented in healthy rats did not provide detectable metabolic products (FIG. 13B), the appearance of $^{15}$N-HBCP peak indicates in vivo reaction of $^{15}$N-BBCP with $H_2O_2$. However, $^{15}$N-CP was not observed, in which the low reaction conversion may be attributed to rapid antioxidant responses in vivo that lowers accessible $H_2O_2$.

$^{15}$N-BBCP is the first designed reaction-based hyperpolarized $^{15}$N-probe with in vivo study performed using a conventional clinical system. While a larger chemical shift difference is highly desired due to the low gyromagnetic ratio of $^{15}$N, both in vitro and in vivo results suggest that $^{15}$N-probes can be utilized to detect 1 ppm or less of chemical shift difference at 3 T. Imaging approach may improve spectral separation of $^{15}$N-BBCP and $^{15}$N-HBCP as compared with MRS, and signal-to-noise ratio may be adjusted.

In vivo application of hyperpolarized $^{15}$N-BBCP to scavenge $H_2O_2$ demonstrated its conversion to $^{15}$N-HBCP but did not detect $^{15}$N-CP under tested conditions, which may be due to the limited concentration of $H_2O_2$. Pathological conditions that persist elevated levels of $H_2O_2$ or an oxidative burst may produce detectable amount of $^{15}$N-CP. The in vivo efficacy of hyperpolarized $^{15}$N-BBCP as a $H_2O_2$-sensing probe in disease models or under chemical stimulation that induces high $H_2O_2$ production (such as a cancer treated with β-lapachone) may be validated using similar experiments as described herein.

In summary, $^{15}$N-BBCP as a novel reaction-based $H_2O_2$ sensing probe using hyperpolarized MRSI was designed and characterized. Currently, hyperpolarized $^{15}$N-probes for in vivo imaging have been largely unexplored. The present disclosure demonstrates the first designed reaction-based $^{15}$N-molecular probe that has been applied in vivo. The probe exhibited ideal properties, including high aqueous solubility, stability, low cytotoxicity, and rapid reaction kinetics. In addition, $^{15}$N-BBCP retained a long polarization lifetime that allowed chemical-shift imaging studies to monitor the reaction with $H_2O_2$. Notably, the presented work demonstrates the possibilities of using reaction-based $^{15}$N-probes to image and characterize oxidative stress for future diagnostic and therapeutic applications.

The foregoing description of the specific aspects will so fully reveal the general nature of the invention that others can, by applying knowledge within the skill of the art, readily modify and/or adapt for various applications such specific aspects, without undue experimentation, without departing from the general concept of the present disclosure. Therefore, such adaptations and modifications are intended to be within the meaning and range of equivalents of the disclosed aspects, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

All publications, patents, patent applications, and/or other documents cited in this application are incorporated by reference in their entirety for all purposes. The breadth and scope of the present disclosure should not be limited by any of the above-described exemplary aspects, but should be defined only in accordance with the following claims and their equivalents.

The invention claimed is:

1. A compound of Formula (I), or a salt thereof,

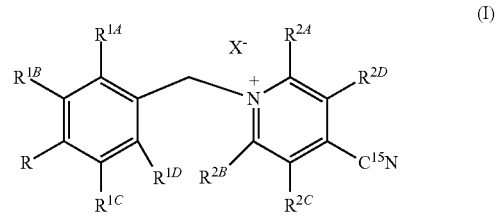

wherein $R^{1A}$, $R^{1B}$, $R^{1C}$, $R^{1D}$, $R^{2A}$, $R^{2B}$, $R^{2C}$, and $R^{2D}$ are each independently H, CHO, COOH, $SO_3H$, CN, $NO_2$, or $NR^xR^y$;

R is a sensing moiety;

$R^x$ and $R^y$ are each independently H or $C_{1-4}$ alkyl; and

X is a counterion.

2. The compound of claim 1, or a salt thereof, wherein R is (R'O)₂B—,

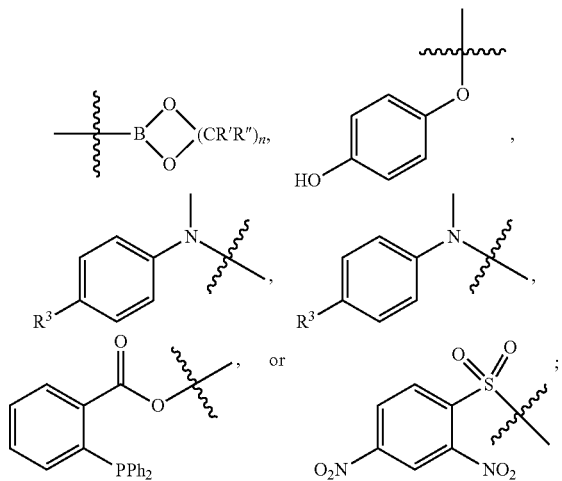

R' is $C_{1-4}$ alkyl;
R' and R" at each occurrence are independently H or $C_{1-4}$ alkyl;
$R^3$ is OH, $OCH_3$, or $NH_2$; and
n is 2 or 3.

3. The compound of claim 2, or a salt thereof, wherein R is

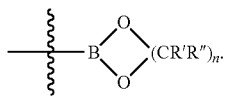

4. The compound of claim 3, or a salt thereof, wherein R is

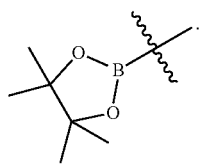 [SMILES: *B1OC(C)(C)C(C)(C)O1]

5. The compound of claim 4, or a salt thereof, which is

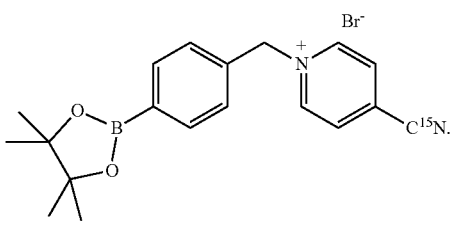

6. An imaging composition comprising an effective amount of a compound of claim 1, or a salt thereof, and at least one additional agent.

7. The imaging composition of claim 6, wherein the at least one additional agent comprises a polarizing agent.

8. A pharmaceutical composition comprising an effective amount of a compound of claim 1, or a pharmaceutically acceptable salt thereof, and a pharmaceutically acceptable carrier.

9. A method of analyzing a reactive species in a sample, the method comprising:
   contacting the sample with an effective amount of a compound of claim 1, or a salt thereof, thereby the reactive species reacts with the compound to produce a product comprising $^{15}N$; and
   detecting the compound and/or the product, thereby detecting the reactive species in the sample.

10. The method of claim 9, further comprising quantitating the reactive species.

11. The method of claim 9, wherein detecting the compound and/or the product comprises detecting the compound and/or the product by magnetic resonance.

12. The method of claim 11, further comprising imaging the compound or and/or the product.

13. The method of claim 12, wherein the imaging comprises magnetic resonance imaging (MRI) or magnetic resonance spectroscopic imaging (MRSI).

14. The method of claim 9, wherein the sample is a cell, optionally wherein the cell is live cell.

15. The method of claim 9, wherein the reactive species comprise a reactive oxygen species, a reactive nitrogen species, or a combination thereof.

16. The method of claim 15, wherein the reactive species is a reactive oxygen species, optionally wherein the reactive oxygen species is hydrogen peroxide.

17. The method of claim 9, wherein the compound is

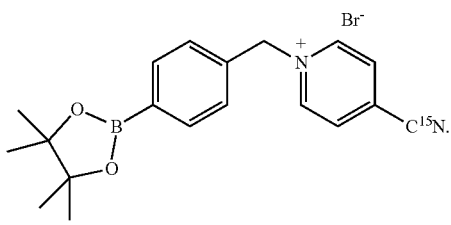

18. The method of claim 9, wherein the product is

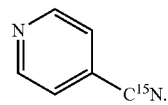

19. A method of imaging a reactive oxygen species in a sample, comprising:
   contacting the sample with an effective amount of a compound of claim 1, or a salt thereof, thereby the reactive oxygen species reacts with the compound to produce a product comprising $^{15}N$; and
   imaging the compound or and/or the product using magnetic resonance imaging (MRI) or magnetic resonance spectroscopic imaging (MRSI).

20. A method of diagnosing a disease associated with a reactive species in a subject, the method comprising:
   administering an effective amount of a compound of claim 1, or a salt thereof, to the subject, thereby the reactive species, if present, reacts with the compound to produce a product comprising $^{15}N$;

detecting the compound and/or the product, thereby determining an amount the reactive species in the subject; and determining a status of the disease according to the amount the reactive species in the subject.

21. The method of claim 20, wherein the reactive species is a reactive oxygen species, optionally wherein the reactive oxygen species is hydrogen peroxide.

22. The method of claim 21, wherein the disease is associated with elevated level of hydrogen peroxide, optionally wherein the disease is cancer, inflammatory disease, aging, cardiovascular disease, diabetes, neurodegenerative disease, stroke, tissue injury, acute lung injury (ALI), chronic lung allograft dysfunction, oxidative stress-induced inflammation within lungs, tissue inflammation, asthma, psoriasis, rheumatoid arthritis, systemic lupus erythematosus (SLE).

* * * * *